US011001838B2

(12) United States Patent
Lee et al.

(10) Patent No.: US 11,001,838 B2
(45) Date of Patent: May 11, 2021

(54) PLATFORM FOR SCREENING PHOSPHOMEVALONATE DECARBOXYLASE

(71) Applicants: Taek Soon Lee, Berkeley, CA (US); Aram Kang, Richmond, CA (US)

(72) Inventors: Taek Soon Lee, Berkeley, CA (US); Aram Kang, Richmond, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/943,632

(22) Filed: Apr. 2, 2018

(65) Prior Publication Data

US 2018/0362970 A1    Dec. 20, 2018

Related U.S. Application Data

(60) Provisional application No. 62/480,279, filed on Mar. 31, 2017.

(51) Int. Cl.
*C12N 15/10*    (2006.01)
*C12N 15/01*    (2006.01)
*C12N 9/88*    (2006.01)

(52) U.S. Cl.
CPC ........... *C12N 15/1079* (2013.01); *C12N 9/88* (2013.01); *C12N 15/01* (2013.01); *C12Y 401/01033* (2013.01)

(58) Field of Classification Search
None
See application file for complete search history.

(56) References Cited

PUBLICATIONS

Atsumi et al., "Non-fermentative pathways for synthesis of branched-chain higher alcohols as biofuels." Nature, 451, 86-90 (2008).
Barta et al., "Structural basis for nucleotide binding and reaction catalysis in mevalonate diphosphate decarboxylase.", Biochemistry. 51, 5611-21 (2012).
Barta et al., Crystal structures of Staphylococcus epidermidis mevalonate diphosphate decarboxylase bound to nhibitory analogs reveal new insight into substrate binding and catalysis. J Biol Chem. 286, 23900-10 (2011).
Beller et al., "Natural products as biofuels and bio-based chemicals: fatty acids and isoprenoids." Nat Prod Rep. 32, 1508-26 (2015).
Bonanno et al., "Structural genomics of enzymes involved in sterol/isoprenoid biosynthesis.", Proc Natl Acad Sci U S A. 98, 12896-901 (2001).
Chen et al., "Characterization of thermophilic archaeal isopentenyl phosphate kinases." Biochemistry. 49, 207-17 (2010).
Chou et al., "Synthetic pathway for production of five-carbon alcohols from isopentenyl diphosphate." Applied and environmental microbiology. 78, 7849-55 (2012).
Cohen, "Functional linkage between genes that regulate osmotic stress responses and multidrug resistance transporters: challenges and opportunities for antibiotic discovery." Antimicrob. Agents Chemother., vol. 58, pp. 640-646 (2014).
Funke et al., "Bioprocess control in microscale: scalable fermentations in disposable and user-friendly microfluidic systems." Microb Cell Fact. 9, 86 (2010).
George et al., "Correlation analysis of targeted proteins and metabolites to assess and engineer microbial isopentenol Droduction." Biotechnology and bioengineering. 111, 1648-58 (2014).
George et al., "Metabolic engineering for the high-yield production of isoprenoid-based C(5) alcohols in *E coli*.", Sci Rep. 5, 11128 (2015).
Gogerty et al., "Formation of isobutene from 3-hydroxy-3-methylbutyrate by diphosphomevalonate decarboxylase." Applied and environmental microbiology. 76, 8004-10 (2010).
Heuston et al., "Isoprenoid biosynthesis in bacterial pathogens." Microbiology. 158, 1389-401 (2012).
Krepkiy et al., "Identification of active site residues in mevalonate diphosphate decarboxylase: implications for a family of phosphotransferases." Protein Sci. 13, 1875-81 (2004).
Krepkiy et al., "Investigation of the functional contributions of invariant serine residues in yeast mevalonate liphosphate decarboxylase." Biochemistry. 44, 2671-7 (2005).
Lange, "Isopentenyl diphosphate biosynthesis via a mevalonate-independent pathway: isopentenyl monophosphate kinase catalyzes the terminal enzymatic step." Proc Natl Acad Sci U S a. 96, 13714-9 (1999).
Lee et al. "BglBrick vectors and datasheets: A synthetic biology platform for gene expression." J Biol Eng. 5, 12 (2011).
Liu et al., "MEP pathway-mediated isopentenol production in metabolically engineered *Escherichia coli*." Microb Cell Fact. 13 (2014).
Martin et al., "Engineering a mevalonate pathway in *Escherichia coli* for production of terpenoids." Nat Biotechnol. 21, 196-802 (2003).
Martinez et al., "Mutation frequencies and antibiotic resistance." Antimicrob Agents Chemother. 44, 1771-7 (2000).
McCullum et al., "Random mutagenesis by error-prone PCR." Methods Mol Biol. 634, 103-9 (2010).
Packer et al., "Methods for the directed evolution of proteins." Nat Rev Genet. 16, 379-94 (2015).
Saraste et al., "The P-loop—a common motif in ATP- and GTP-binding proteins." Trends Biochem Sci. 15, 430-4 (1990).
Sun et al., "ATP requirement for acidic resistance in Escherichia coli." J Bacteriol. 193, 3072-7 (2011).

(Continued)

*Primary Examiner* — Rebecca E Prouty
(74) *Attorney, Agent, or Firm* — Robin C. Chiang; Lawrence Berkeley National Laboratory

(57) ABSTRACT

The present invention provides for a method to identify a second or mutant phosphomevalonate decarboxylase (PMD) with a higher PMD activity compared to a first PMD, comprising (a) culturing a medium comprising a first host cell expressing the first PMD and a second host cell expressing the second or mutant PMD wherein the first and second host cells have their respective PMD enzymatic activities coupled to the growth rates of the host cells, and (b) identifying the second host cell that has a higher growth rate than the first host cell, thereby identifying the second or mutant PMD having a higher PMD activity.

4 Claims, 15 Drawing Sheets

Specification includes a Sequence Listing.

(56) References Cited

PUBLICATIONS

Weerasinghe et al., "Simulation of structural and functional properties of mevalonate diphosphate decarboxylase (MVD)." J Mol Model. 16, 489-98 (2010).

Zhang et al., "A second target of the antimalarial and antibacterial agent fosmidomycin revealed by cellular metabolic profiling." Biochemistry, 50, 3570-7 (2011).

Hengge, "The two-component network and the general stress sigma factor RpoS (sigma S) in Escherichia coli." Adv Exp Med Biol. 631, 40-53 (2008).

George et al., "Isoprenoid drugs, biofuels, and chemicals--artemisinin, farnesene, and beyond." Adv Biochem Eng Eliotechnol. 148, 355-89 (2015).

Kang et al., "Isopentenyl diphosphate (IPP)-bypass mevalonate pathways for isopentenol production." Metab Eng. 34, 25-35 (2016).

Mack et al., "Investigation of biofuels from microorganism metabolism for use as anti-knock additives." Fuel. 117, 939-943 (2014).

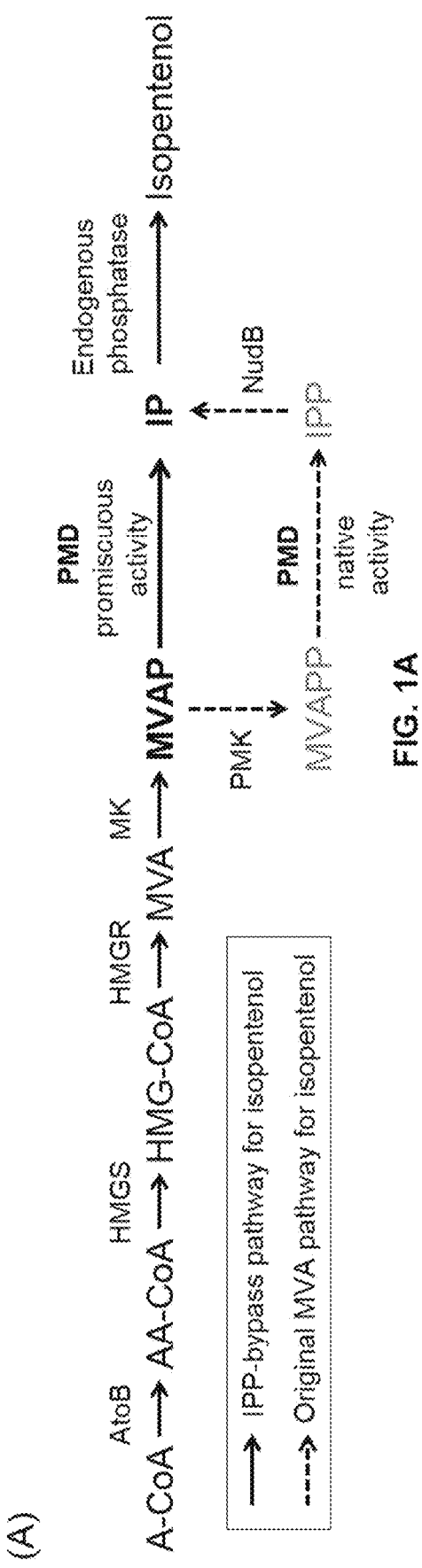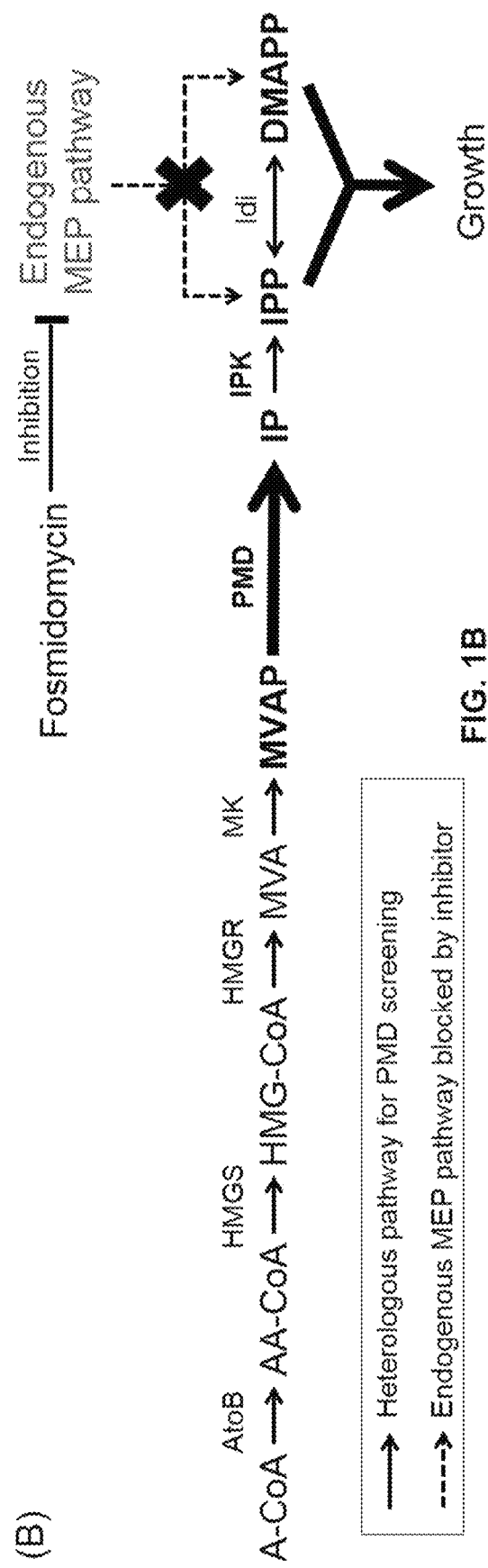
FIG. 1A
FIG. 1B

```
Seq_1    3  VYTASVTAPVNIATLKYWCKRDTKLNLPTNSSISVTLSQDDLRTLTSAATAPEFERDTLM   62
              V +    A  NIA +KYWCK D   +P N+S+SVTL  D   T  T   P+F  D L
Seq_2    2  VKSGKARAHTNIALIKYWGKADETYIIPMNNSLSVTL---DRFYTETKVTFDPDETEDCLI  59

Seq_1   63  LNG-EPHSIDNERTQNCLRDLRQLRKEMESKDASLPTLSQWKLH---IVSENNFPTAAGLA  119
              LNG E +++   +  QN +   +R  L
Seq_2   60  LNGNEVNAREKEKTQNYMNIVRDLAGN------+LH  I SEN  PTAAGLA
                                              RLHARIESENYVPTAAGLA        105

Seq_1  120  SSAAGFAALVSAIAKLYQLPQSTSEISRIARKGSGSACRSLFGGYVAWEMCKAEDGHDSM  179
              SSA+ +AAL +A    L  S   +++SR+AR+GSGSA  RS+FCG+   W    E GHD +
Seq_2  106  SSASAYAALAAACNEALSLNLSDTDLSRLARRGGSASRSIFCGGFAEW------EKGHDDL  160

Seq_1  180  A--VQIADSSDWPQ-MKKACVLVVSDIKHDVSSHDGMQLTVA+SELFKERIEHVVPKRFEV  236
              +S+ W + +           +V+++    K  VS+  GM LT  TS    +++  ++HV
Seq_2  161  TSYAHCINSNGWEKDLSMIFVVINNQSIKVSSGCMSLTRDTSRFYQYMLDHVDEDLNEA   220

Seq_1  237  MRKAIVEKDFEATFAKETMMDSNSFHATCLDSFPIFYMNDTS----KRIISWCHTINQFYG  293
                       +  +      +             HAT L + PP  Y+    S    I+    C    N
Seq_2  221  --KEAVKNQDFQRLGEVTEANGLRMHATNLGAQPPFTYLVQESYDAMAIVEQCRKAN---  275

Seq_1  294  ETTVAYTFDAGPNAVLYYLAENESKLFAFIYKLF  327
              +T DAGPN   +        +N+  +         K+F
Seq_2  276  -LPCYFTMDAGPNVKVLVEKKNKQAVMEQFLKVF  308
```

PLATFORM FOR SCREENING PHOSPHOMEVALONATE DECARBOXYLASE

RELATED PATENT APPLICATIONS

The application claims priority to U.S. Provisional Patent Application Ser. No. 62/480,279, filed Mar. 31, 2017, which is herein incorporated by reference in its entirety.

STATEMENT OF GOVERNMENTAL SUPPORT

The invention was made with government support under Contract Nos. DE-AC02-05CH11231 awarded by the U.S. Department of Energy. The government has certain rights in the invention.

FIELD OF THE INVENTION

The present invention is in the field of producing isopentenol.

BACKGROUND OF THE INVENTION

Isopentenol (or isoprenol, 3-methyl-3-buten-1-ol) is a promising biofuel and a precursor for industrial chemicals such as isoprene (Beller et al., 2015; George et al., 2015a). The research octane number of isopentenol (98) is close to isooctane (RON=100), demonstrating its potential use as an anti-knocking additive in gasoline (Liu et al., 2014; Mack et al., 2014). Several microbial hosts have been engineered for biological production of isopentenol with the most commonly targeted pathways including isoprenoid pathways from both the mevalonate (MVA) pathway and the methylerythritol phosphate (MEP) pathway, and the keto acid pathway (Atsumi et al., 2008).

Briefly, the conventional MVA pathway for isopentenol production starts with reactions that condense three acetyl-CoA molecules and produce one molecule of MVA. Next, mevalonate kinase (MK) phosphorylates MVA to mevalonate 5-phosphate (MVAP), which is subsequently phosphorylated to mevalonate 5-diphosphate (MVAPP, also diphosphomevalonate) by 5-phosphomevalonate kinase (PMK). The phosphorylation reactions consume two adenosine triphosphate (ATP) molecules, and then diphosphomevalonate decarboxylase (PMD) converts MVAPP to isopentenyl diphosphate (IPP) while consuming one additional ATP molecule (FIG. 1A). Lastly, isopentenol is produced by hydrolysis of the pyrophosphate group from IPP (Chou and Keasling, 2012).

Extensive optimization of the conventional MVA pathway for isopentenol production in *Escherichia coli* resulted in titers of 2.2 g/L with 70% of apparent theoretical yield (George et al., 2014; George et al., 2015b). However, the "IPP-dependency" of the conventional MVA pathway intrinsically limits engineering of the MVA pathway toward high titer isopentenol production for two primary reasons: its high ATP requirement and toxicity of IPP (Kang et al., 2016). First, generation of one molecule of IPP via the MVA pathway requires the consumption of 3 ATP molecules, which accounts for approximately 5.3% of the theoretical ATP yield from complete aerobic respiration of one and half (1.5) molecules of glucose. However, in the conventional MVA-based isopentenol production pathway, the hydrolysis of the diphosphate group of IPP squanders cellular ATP, underscoring the importance of constructing more energetically efficient pathways for isopentenol production. Secondly, accumulation of IPP has been proposed to inhibit growth of *E. coli* (George et al., 2015b; Kang et al., 2016; Martin et al., 2003). Although specific molecular mechanisms behind the growth inhibition effects of IPP are not clear yet, general stress responses accompanied with the growth inhibition potentially divert carbon flux away from desired isopentenol production (Adolfsen and Brynildsen, 2015; Cohen, 2014; Hengge, 2008; Kang et al., 2016; Sun et al., 2011).

SUMMARY OF THE INVENTION

The present invention provides for a method to identify a second or mutant phosphomevalonate decarboxylase (PMD) with a higher PMD activity compared to a first PMD, comprising (a) culturing a medium comprising a first host cell expressing the first PMD and a second host cell expressing the second or mutant PMD wherein the first and second host cells have their respective PMD enzymatic activities coupled to the growth rates of the host cells, and (b) identifying the second host cell that has a higher growth rate than the first host cell, thereby identifying the second or mutant PMD having a higher PMD activity.

In some embodiments, the PMD enzymatic activity of a host cell is coupled to the growth rates of the host cell by blocking isopentenyl pyrophosphate (IPP) production via the 2-C-methyl-D-erythritol 4-phosphate (MEP) pathway and increasing the enzymatic activities of IP kinase, such that IPP is produced from phosphomevalonate (MVAP) provided via the mevalonate (MVA) pathway.

The present invention provides for a polypeptide comprising an amino acid sequence having a sequence identity equal to or more than 70% of SEQ ID NO:1 or SEQ ID NO:2, and comprising one or more amino acid residue substitution described herein which increases the PMD activity. In some embodiments, the amino acid residue substitution is shown in FIG. 2A to FIG. 4C, FIG. 11, and described in Example 1 herein, such as R74S, I145A, and M212Q, and any double or triple combination thereof. The present invention provides for a polypeptide comprising an amino acid sequence having a sequence identity equal to or more than 70% of SEQ ID NO:1 or SEQ ID NO:2, and comprising one or more of the following corresponding substitutions: R74S, I145A, and M212Q (for SEQ ID NO:1), and any double or triple combination thereof.

In some embodiments, the polypeptide comprises an amino acid sequence having a sequence identity equal to or more than 70% of SEQ ID NO:1, and comprising one or more of the following substitutions: R74S, I145A, and M212Q, or any double or triple combination thereof. In some embodiments, the polypeptide comprises an amino acid sequence having a sequence identity equal to or more than 70% of SEQ ID NO:2, and comprising one or more of the following substitutions: K72S, L131A, and M196Q, or any double or triple combination thereof.

The present invention also provides for a method of constructing the polypeptide of the present invention.

BRIEF DESCRIPTION OF THE DRAWINGS

The foregoing aspects and others will be readily appreciated by the skilled artisan from the following description of illustrative embodiments when read in conjunction with the accompanying drawings.

FIG. 1. Schematic diagrams of (A) the IPP-bypass isopentenol pathway catalyzed by AtoB, HMGS, HMGR, MK and PMD (solid arrows) and three reactions by PMK, PMD and NudB (dotted arrows) included in the original MVA pathway, and (B) design of the pathways for screening platform, which includes IP kinase (IPK) and IPP isomerase (Idi) in addition to 5 reactions in IPP-bypass isopentenol pathway. Abbreviations: Ac-CoA, acetyl-CoA; AAc-CoA, acetoacetyl-CoA; HMG-CoA, 3-hydroxy-3-methyl-glutaryl-CoA; MVA, mevalonate; MVAP, mevalonate phosphate; MVAPP, mevalonate diphosphate; IPP, isopentenyl diphosphate; IP, isopentenyl monophosphate.

FIG. 12. Amino acid sequence comparison between *Saccharomyces cerevisiae* PMD (Seq_1, SEQ ID NO:1) and *Staphylococcus epidermidis* PMD (Seq_2, SEQ ID NO:2).

DETAILED DESCRIPTION OF THE INVENTION

Figure 2A:
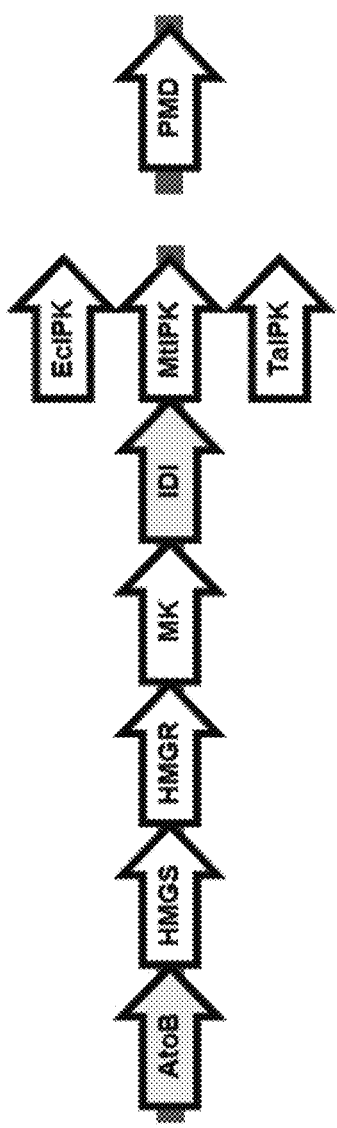
FIG. 2. Development and optimization of the screening platform (A) Test of three isopentenyl phosphate (IP) kinases with wild type PMDsc (WT) or S208E mutant: EcIPK, IP kinase from *E. coli*; MtIPK, IP kinase from *Methanothermobacter thermautotrophicus*; Ta IPK, IP kinase from *Thermoplasma acidophilum*. Two concentrations of aTc (10 nM and 100 nM) were used for expression of PMD genes. (B) Test of four PMDsc sequences (WT, K22M, R74H and S208E) with MtIPK. Expression of four PMDsc mutants were induced by 10 mM arabinose. Relative growth rate ($h^{-1}$) and relative activity were on the table. Shaded area is standard error of four biological replicates.
Figure 2A:
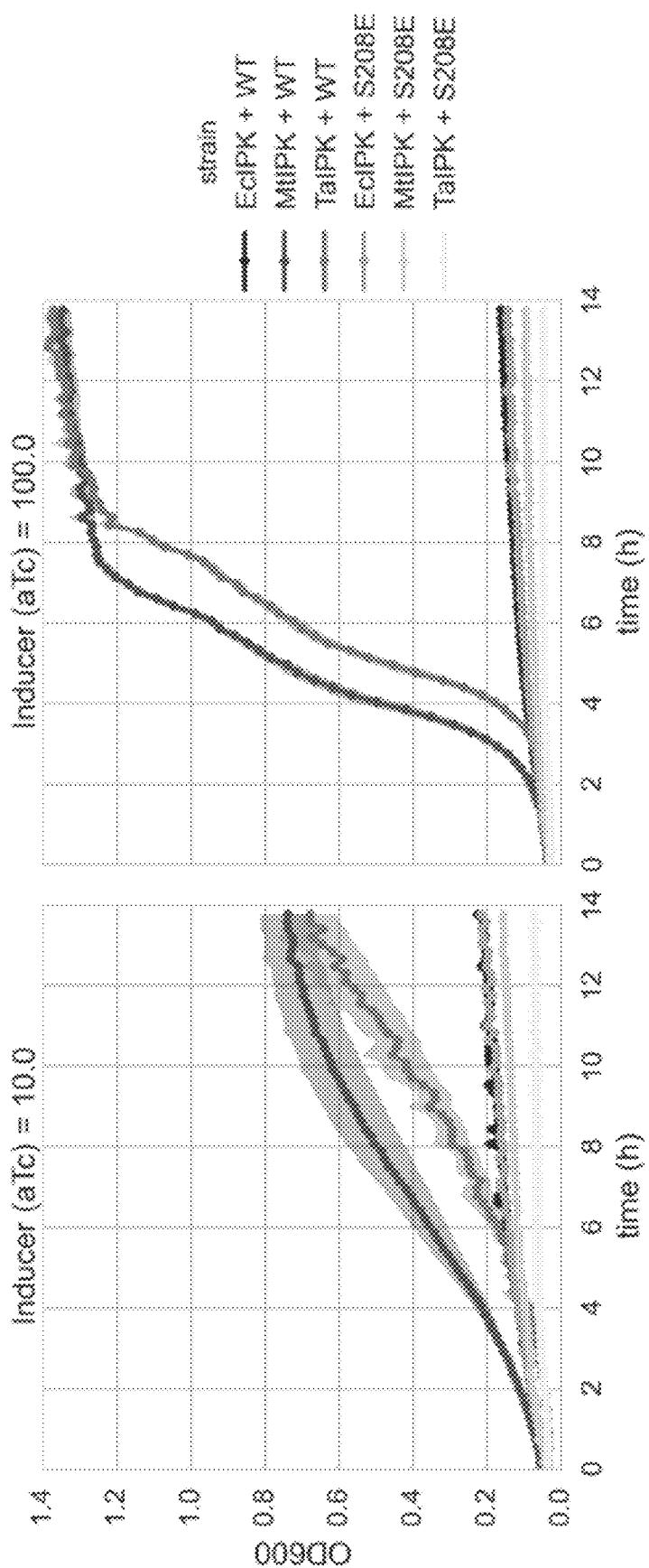

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "enzyme" includes a single enzyme as well as a plurality of enzymes, either the same (e.g., the same molecule) or different.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The terms "host cell" and "host microorganism" are used interchangeably herein to refer to a living biological cell that can be transformed via insertion of an expression vector. Thus, a host organism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus.

The term "heterologous" as used herein refers to a composition, such as enzyme or nucleic acid, or the like, that in nature is not found together with another composition. For example, an enzyme is heterologous to a host cell, if in nature the species of the host cell does not have the enzyme.

The term "heterologous DNA" as used herein refers to a polymer of nucleic acids wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Specifically, the present invention describes the introduction of an expression vector into a host microorganism, wherein the expression vector contains a nucleic acid sequence coding for an enzyme that is not normally found in a host microorganism. With reference to the host microorganism's genome, then, the nucleic acid sequence that codes for the enzyme is heterologous.

The term "mevalonate pathway" is used herein to refer to the pathway that converts acetyl-CoA to isopentenyl pyrophosphate through a mevalonate intermediate.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "transduce" as used herein refers to the transfer of a sequence of nucleic acids into a host microorganism or cell. Only when the sequence of nucleic acids becomes stably replicated by the cell does the host microorganism or cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a host microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; intemucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., arninoalklyphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (*Biochem.* 9:4022, 1970).

The term "operably linked" refers to a functional linkage between a nucleic acid expression control sequence (such as a promoter) and a second nucleic acid sequence, wherein the expression control sequence directs transcription of the nucleic acid corresponding to the second sequence.

The term "substantially identical" describes an amino acid sequence that is at least 70%, 75%, 80%, 85%, 90%, 95% or 99% identical to any one of the amino acid sequence described herein. The "substantially identical" amino acid sequence may retain amino acids residues that are recognized as conserved for the enzyme, and may have non-conserved amino acid residues substituted or found to be of a different amino acid, or amino acid(s) inserted or deleted, but which does not affect or has insignificant effect its enzymatic activity, as compared to the enzyme described herein. The "substantially identical" enzyme has an enzymatic activity that is identical or essentially identical to the biological activity of the regulator or enzyme described herein. The "substantially identical" enzyme may be found in nature, i.e. naturally occurring, or be an engineered mutant thereof.

The PMD is any suitable PMD, such as any PMD with an amino acid sequence substantially identical to the amino acid sequences of SEQ ID NO: 1 or 2. The substantially identical PMD comprises one or more, or all, of the conserved or identical residues identified in FIG. 12, including but not limited to one or more, or all, of the conserved/identical residues indicated by a star.

The host cell can be a eukaryote or prokaryote cell that produces acetyl-CoA. Any prokaryotic or eukaryotic host cell may be used in the present method so long as it remains viable after being transformed with a sequence of nucleic acids. Generally, although not necessarily, the host cell is bacterial. Examples of bacterial host cells include, without limitation, those species assigned to the *Escherichia, Enterobacter, Azotobacter, Erwinia, Bacillus, Pseudomonas, Klebsielia, Proteus, Salmonella, Serratia, Shigella, Rhizo-* bia, *Vitreoscilla*, *Paracoccus*, and *Clostridia* taxonomical classes. Preferably, the host cell is not adversely affected by the transduction of the necessary nucleic acid sequences, the subsequent expression of the proteins (i.e., enzymes), or the resulting intermediates required for carrying out the steps associated with the mevalonate pathway. For example, it is preferred that minimal "cross-talk" (i.e., interference) occur between the host cell's own metabolic processes and those processes involved with the mevalonate pathway.

Suitable eukaryotic cells include, but are not limited to, fungal, insect or mammalian cells. Suitable fungal cells are yeast cells, such as yeast cells of the *Saccharomyces* genus.

The present invention provides for a method to identify a second or mutant phosphomevalonate decarboxylase (PMD) with a higher PMD activity compared to a first PMD, comprising (a) culturing a medium comprising a first host cell expressing the first PMD and a second host cell expressing the second or mutant PMD wherein the first and second host cells have their respective PMD enzymatic activities coupled to the growth rates of the host cells, and (b) identifying the second host cell that has a higher growth rate than the first host cell, thereby identifying the second or mutant PMD having a higher PMD activity.

In some embodiments, the culturing step comprises the host cells for a plurality of generations. In some embodiments, the plurality of generations is equal to or more than 2, 3, 4, 5, 6, 7, 8, 9, or 10 generations of the fastest growing host cell in the medium. In some embodiments, the first and/or second PMDs are naturally occurring or mutant PMDs.

In some embodiments, the PMD enzymatic activity of a host cell is coupled to the growth rates of the host cell by blocking isopentenyl pyrophosphate (IPP) production via the 2-C-methyl-D-erythritol 4-phosphate (MEP) pathway and increasing the enzymatic activities of IP kinase, such that IPP is produced from phosphomevalonate (MVAP) provided via the mevalonate (MVA) pathway.

Isopentenol (3-methyl-3-butenol) is a promising biofuel and a precursor for industrial chemicals such as isoprene. Two biological pathways have been engineered for isopentenol production: isoprenoid pathways and keto acid pathways. The highest titers and yield have been achieved by engineering the mevalonate (MVA) pathway in *E. coli* and subsequent extensive optimization of the pathway based on analysis of intermediates and enzyme expression levels. However, MVA pathway has intrinsic limitations for improved isopentenol production: it accumulates a toxic intermediate, isopentenyl pyrophosphate (IPP), of which biosynthesis is ATP-demanding and requires highly aerated fermentation conditions. To overcome the limitations of the original MVA pathway for isopentenol production, we have engineered IPP-bypassing MVA pathway to produce isopentenol in *E. coli* (Kang 2015, FIG. 11). The IPP-bypassing MVA pathway relied on decarboxylation of phosphomevalonate (MVAP) to isopentenyl monophosphate (IP) via promiscuous activity of diphosphomevalonate decarboxylase (PMD). In our previous works, we demonstrated various advantages of the IPP-bypassing pathway over those of the original pathway: reduced IPP toxicity and robust isopentenol production under aeration-limited conditions. However, the decarboxylation activity of PMD for MVAP limits isopentenol production at higher titers. If the IPP-bypassing MVA pathway can be engineered with a better mutant PMD with higher activity for MVAP, the isopentenol titer would be significantly improved than the current titer.

Figure 8:
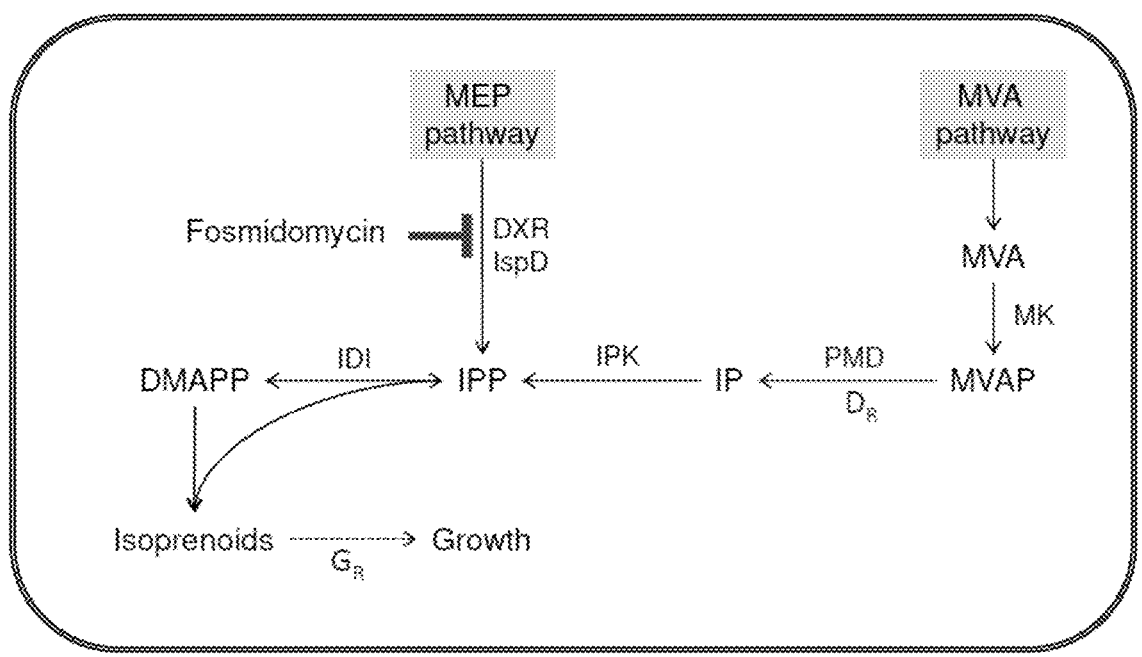
FIG. 8. Schematic diagram of the screening methods. Phosphomevalonate (MVAP)-decarboxylation activity of diphosphomevalonate decarboxylase (PMD, $D_R$) was coupled to growth rate ($G_R$) by expressing mevalonate (MVA) pathway, mevalonate kinase (MK), PMD, IP kinase (IPK) and IPP/dimethylallyl pyrophosphate (DMAPP) isomerase (IDI) while IPP supply via 2-C-methyl-D-erythritol-4-phosphate (MEP) pathway was by fosmidomycin, which inhibits xylulose 5-phosphate reductoisomerase (DXR) or 2-C-methyl-D-erythritol 4-phosphate cytidylyltransferase (IspD).
Figure 9:
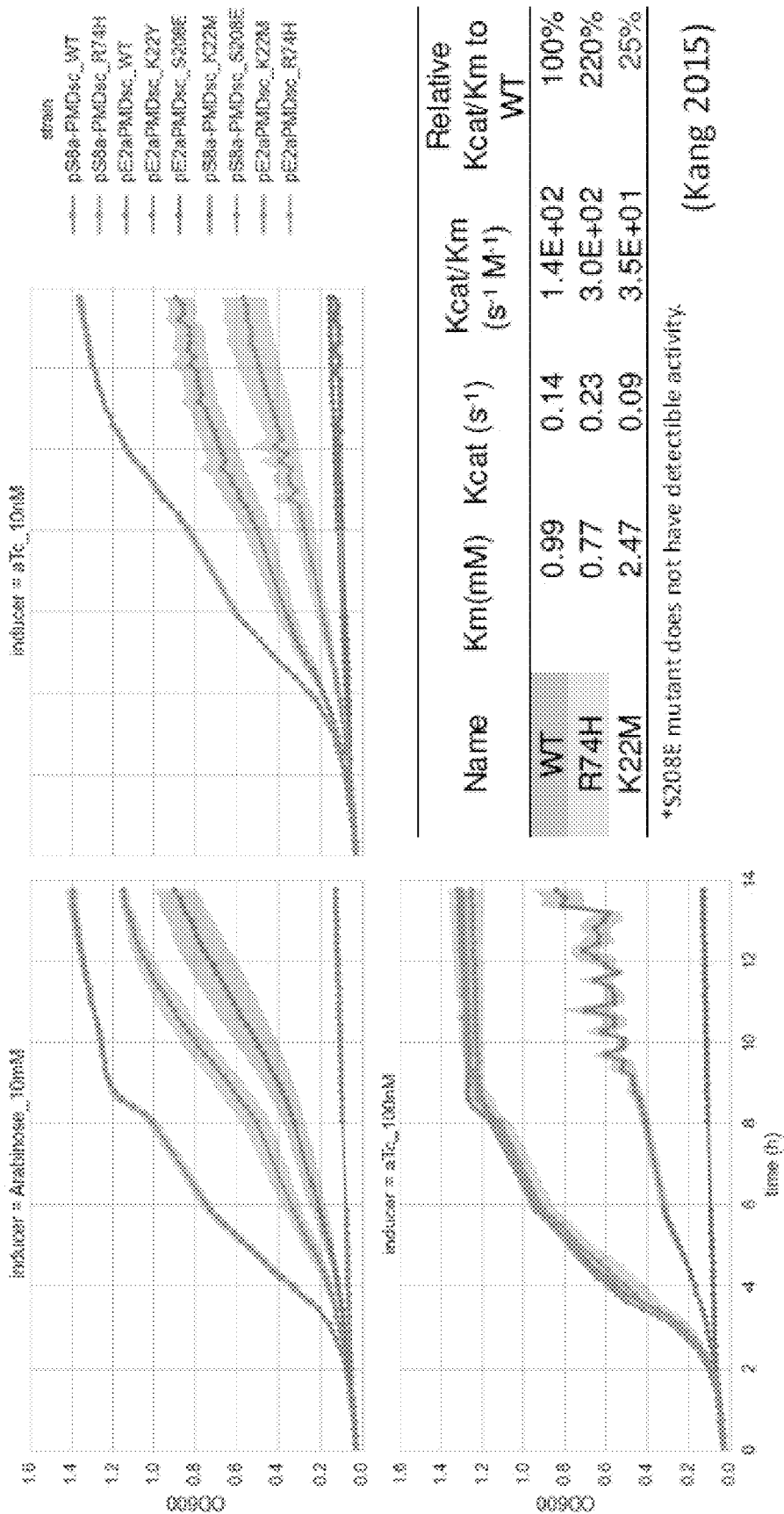
FIG. 9. Validation of the screening platform using mutants with known activity. In a previous study (Kang 2015), three mutants, S208E, K22M and R74H: S208E were identified that completely removed activity (not detectable) while K22M and R74H significantly decreased (25%) or increased (220%) activity of WT for phosphomevalonate (MVAP). Growth of these mutants was tested in two induction system—arabinose-inducible (pS8a) and anhydrotetracycline (aTc)-inducible (pE2a) system, and the pE2a system showed more homogenous PMD expression, which increases sensitivity and robustness of the screening platform. Also, activity of three mutants was verified to show good correlation to growth rate under the screening conditions.
Figure 10:
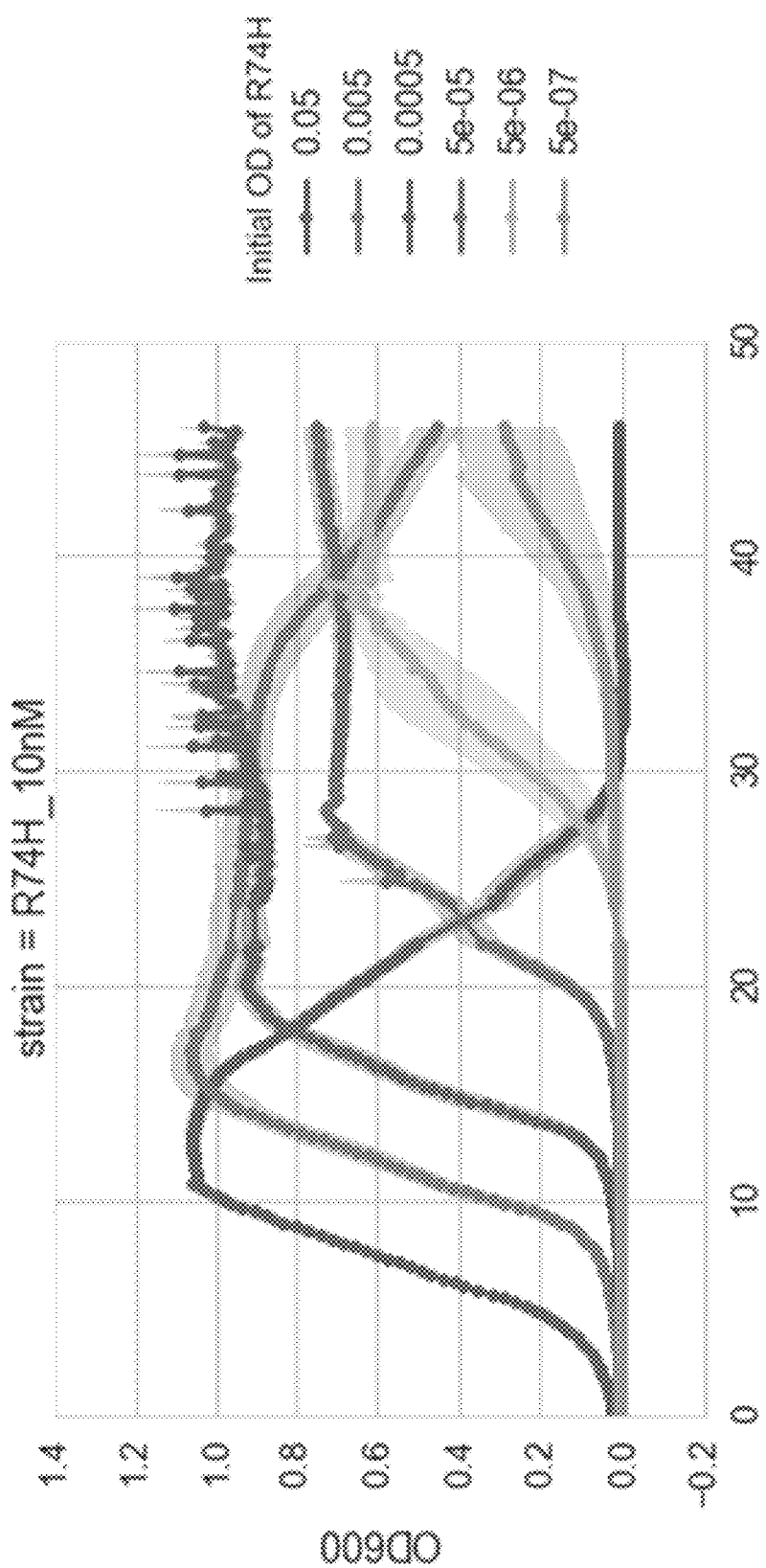
FIG. 10. Optimization of Screening PMD enzyme screening platform.

The present invention provides for a high-throughput method to identify a better decarboxylase for phosphomevalonate (MVAP), which will improve isopentenol production via isopentenyl pyrophosphate (IPP)-bypassing mevalonate (MVA) pathways. In this high-throughput screening platform (FIG. 8), enzymatic activity of diphosphomevalonate decarboxylase (PMD) was coupled to growth rate of *E. coli* DH1, and therefore improved PMD would dominate the population after several passages of dilutions. To couple PMD activity to growth rate, IPP production via 2-C-methyl-D-erythritol 4-phosphate (MEP) was blocked while IP kinase was co-expressed in *E. coli* to supply IPP from IP produced by activity of PMD on MVAP. The screening platform was validated with several PMD mutants, of which activities for MVAP were known, and we observed that growth rate of these mutants were well correlated to their growth rates (FIG. 9). After validating the screening platform, six saturation mutagenesis libraries were tested by the screening platform, and we identified three mutants that significantly improved isopentenol production compared to wild type (FIG. 10).

In this screening platform, PMD mutants with improved activity are selected based on their growth and viability. Selection is a powerful screening approach: it is not necessary to test of an individual design, but designs with desirable activity can be enriched among its diverse population under the selection pressure. Therefore, the screening platform described herein significantly improves efficiency of screening a large size of mutant libraries over the commonly used chromatography-based screening methods (e.g. gas chromatography). In addition, growth-based selection is empowered by supply of IPP, which suggests possible application of this screening platform for other IPP-based isoprenoids pathways to improve carbon flux of glucose to IPP via MVA pathways.

Figure 11:
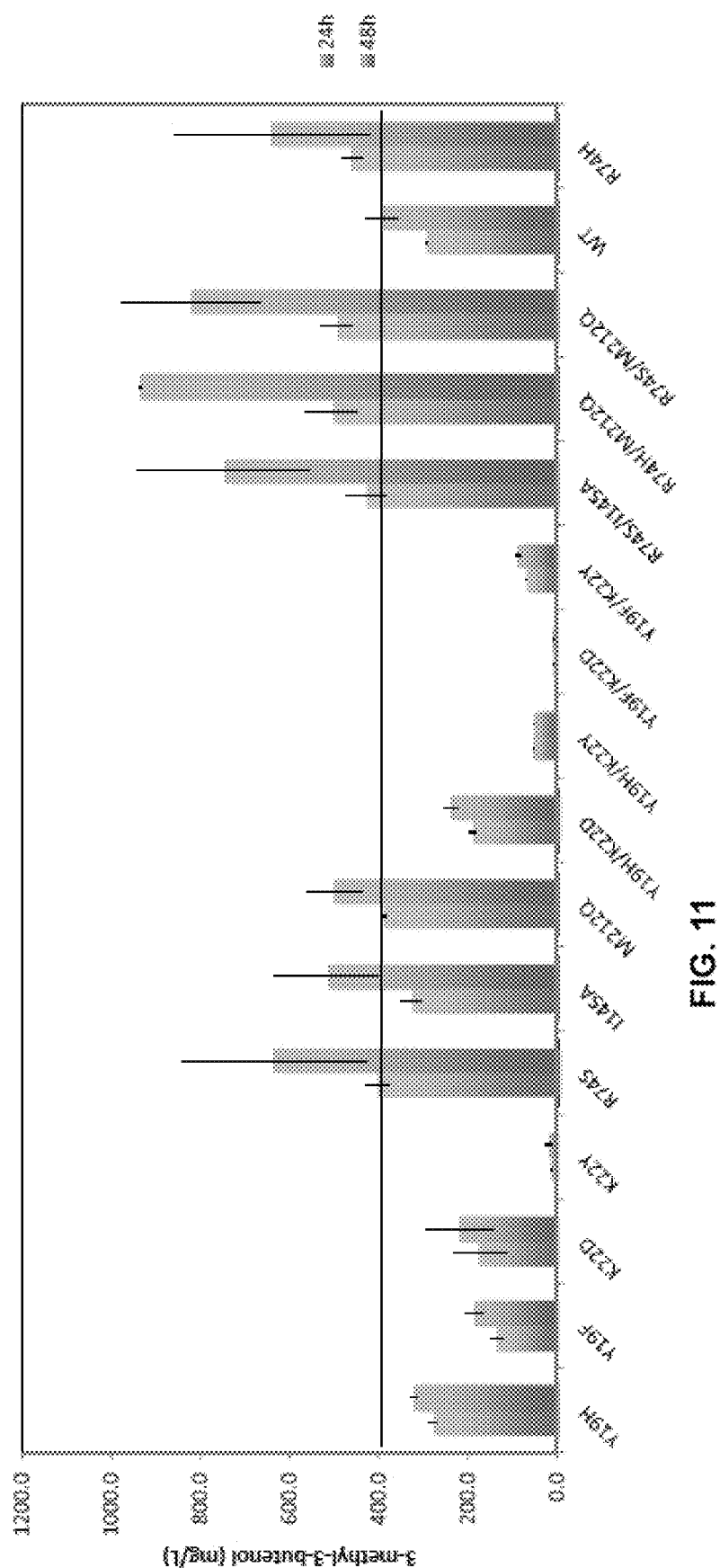
FIG. 11. Mutants identified from saturation mutagenesis library of PMD: higher activity PMD mutants (above the line: R74S, I145A, M212Q) were successfully selected by the screening platform, and their single mutant or double mutants (R74S/I145A, R74H/M212Q, R74S/M212Q) significantly improved isopentenol production via IPP-bypassing mevalonate (MVA) pathway.

The present invention provides for a polypeptide comprising an amino acid sequence having a sequence identity equal to or more than 70% of SEQ ID NO:1 or SEQ ID NO:2, and comprising one or more amino acid residue substitution described herein which increases the PMD activity. In some embodiments, the amino acid residue substitution is shown in FIG. 11, such as R74S, I145A, and M212Q, and any double or triple combination thereof.

The amino acid sequence of *Saccharomyces cerevisiae* diphosphomevalonate decarboxylase (PMD) is as follows:

```
                                            (SEQ ID NO: 1)
         10         20         30         40
MTVYTASVTA PVNIATLKYW GKRDTKLNLP TNSSISVTLS 50         60         70         80
QDDLRTLTSA ATAPEFERDT LWLNGEPHSI DNERTQNCLR 90        100        110        120
DLRQLRKEME SKDASLPTLS QWKLHIVSEN NFPTAAGLAS 130        140        150        160
SAAGFAALVS AIAKLYQLPQ STSEISRIAR KGSGSACRSL 170        180        190        200
FGGYVAWEMG KAEDGHDSMA VQIADSSDWP QMKACVLVVS 210        220        230        240
DIKKDVSSTQ GMQLTVATSE LFKERIEHVV PKRFEVMRKA 250        260        270        280
IVEKDFATFA KETMMDSNSF HATCLDSFPP IFYMNDTSKR 290        300        310        320
IISWCHTINQ FYGETIVAYT FDAGPNAVLY YLAENESKLF
```

```
              330         340         350         360
        AFIYKLFGSV  PGWDKKFTTE  QLEAFNHQFE  SSNFTARELD 370         380         390
        LELQKDVARV  ILTQVGSGPQ  ETNESLIDAK  TGLPKE
```

The amino acid sequence of *Staphylococcus epidermidis* diphosphomevalonate decarboxylase (PMD) is as follows:

```
                                              (SEQ ID NO: 2)
               10          20          30          40
        MVKSGKARAH  TNIALIKYWG  KADETYIIPM  NNSLSVTLDR 50          60          70          80
        FYTETKVTFD  PDFTEDCLIL  NGNEVNAKEK  EKIQNYMNIV 90         100         110         120
        RDLAGNRLHA  RIESENYVPT  AAGLASSASA  YAALAAACNE 130         140         150         160
        ALSLNLSDTD  LSRLARRGSG  SASRSIFGGF  AEWEKGHDDL 170         180         190         200
        TSYAHGINSN  GWEKDLSMIF  VVINNQSKKV  SSRSGMSLTR 210         220         230         240
        DTSRFYQYWL  DHVDEDLNEA  KEAVKNQDFQ  RLGEVIEANG 250         260         270         280
        LRMHATNLGA  QPPFTYLVQE  SYDAMAIVEQ  CRKANLPCYF 290         300         310         320
        TMDAGPNVKV  LVEKKNKQAV  MEQFLKVFDE  SKIIASDIIS

SGVEIIK
```

The present invention also provides for a genetically modified host cell expressing the polypeptide of the present invention, wherein the host cell has an increased PMD activity. The present invention also provides for a nucleic acid encoding the polypeptide of the present invention. In some embodiments, the nucleic acid is vector capable of stable maintenance in a host cell. The host cell can be a eukaryotic or a prokaryotic cell. The host cell can be an animal or plant cell. The host cell can be a mammalian, insect, or yeast cell. The host cell can be a eubacterial cell, such as *E. coli*. In some embodiments, the vector comprises nucleotide sequences which enable its stable maintenance in the host cell or integration into the genome of the host cell. The nucleic acid can further comprises transcriptional control sequences, such as a promoter, activation sequences, or the like, which enable the expression of the encoded polypeptide in the host cell. One skilled in the art is able to determine what sequences to use in a particular host cell.

The present invention also provides for a method of constructing the polypeptide of the present invention.

Any of the enzymes used in the invention identified herein can be substituted with a polypeptide with an amino acid sequence substantially identical to the enzyme identified.

This invention can use the PMD, and other enzymes and materials, and methods taught in U.S. Provisional Patent Application Ser. No. 62/119,071 and PCT International Patent Application Pub. No. WO 2016/134381, which are both incorporated by reference in their entireties.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

EXAMPLE 1

High-Throughput Enzyme Screening Platform for the IPP-Bypass Mevalonate Pathway for Isopentenol Production Isopentenol (or isoprenol, 3-methyl-3-buten-1-ol) is a drop-in biofuel and a precursor for commodity chemicals such as isoprene. Biological production of isopentenol via the mevalonate pathway has been optimized extensively in *Escherichia coli*, yielding 70% of its theoretical maximum. However, high ATP requirements and isopentenyl diphosphate (IPP) toxicity pose immediate challenges for engineering bacterial strains to overproduce commodities utilizing IPP as an intermediate. To overcome these limitations, an "IPP-bypass" isopentenol pathway was developed using the promiscuous activity of a mevalonate diphosphate decarboxylase (PMD) and demonstrated improved performance under aeration-limited conditions. However, relatively low activity of PMD toward the non-native substrate (mevalonate monophosphate, MVAP) was shown to limit flux through this new pathway. By inhibiting all IPP production from the endogenous non-mevalonate pathway, a high-throughput screening platform was developed that correlated promiscuous PMD activity toward MVAP with cellular growth. Successful identification of mutants that altered PMD activity demonstrated the sensitivity and specificity of the screening platform. Strains with evolved PMD mutants and the novel IPP-bypass pathway increased titers up to 2.4-fold. Further enzymatic characterization of the evolved PMD variants suggested that higher isopentenol titers could be achieved either by altering residues directly interacting with substrate and cofactor or by altering residues on nearby α-helices. These altered residues could facilitate the production of isopentenol by tuning either $k_{cat}$ or $K_i$ of PMD for the non-native substrate. The synergistic modification made on PMD for the IPP-bypass mevalonate pathway is expected to significantly facilitate the industrial scale production of isopentenol.

Since IPP is an essential precursor for isopentenol production in the MVA pathway, maintaining IPP at the optimal level is critical for efficient isopentenol production while minimizing the growth inhibition by excessive IPP. Therefore, "IPP-dependency" of the MVA pathway makes the engineering of the conventional IPP-dependent MVA pathway for isopentenol production more complicated and inefficient.

To overcome the limitations of the IPP-dependent conventional MVA pathway, an IPP-bypass MVA pathway has been developed (Kang et al., 2016) (FIG. 1A). A heterologously expressed *Saccharomyces cerevisiae* PMD enzyme (PMDsc) promiscuously decarboxylates MVAP to form isopentenyl phosphate (IP), which is hydrolyzed to isopentenol by endogenous phosphatases. This novel IPP-bypass MVA pathway significantly reduced IPP toxicity and made isopentenol production more robust relative to the native MVA pathway under aeration-limited conditions by decreasing ATP consumption (Kang et al., 2016). Despite its lower toxicity and higher energetic efficiency, isopentenol production via the IPP-bypass MVA pathway was limited by relatively low activity of PMDsc toward the alternative substrate, MVAP ($k_{cat}$=0.14 sec$^{-1}$) compared to the activity toward MVAPP, the original substrate ($k_{cat}$=5.4 sec$^{-1}$) (Kang et al., 2016; Krepkiy and Miziorko, 2004). Therefore, engineering PMD to be more active toward MVAP is necessary to relieve the bottleneck and increase isopentenol titers and productivity of the IPP-bypass isopentenol pathway.

With this goal, a growth-linked selection method to screen PMD mutants with improved activity toward MVAP was developed. In this new screening platform, PMDsc substrate promiscuity was coupled to the formation of IPP and dimethylallyl pyrophosphate (DMAPP), essential metabolites for *E. coli* growth. IPP production from the endogenous MEP pathway was eliminated by supplementing an antibiotic that inhibits the MEP pathway. *E. coli* growth was rescued only by co-expression of the heterologous IPP-bypass pathway containing sufficiently active PMDsc to convert MVAP to IP with isopentenyl phosphate kinase (IPK), which produces IPP from IP. Using the growth-linked screening platform, libraries of PMD variants were evaluated and mutations were identified that improve isopentenol production in *E. coli* via the IPP-bypass MVA pathway.

Results and Discussion

Design of Screening Platform and Optimization

The screening platform was designed in which the growth rate of the host strain is coupled to the decarboxylation rate of the PMD enzyme (FIG. 1B). To link cellular growth rates directly with MVAP decarboxylation rates, IPP supply via the endogenous MEP pathway should be blocked either by gene knock-out or by the addition of inhibitor of the pathway. Genes involved in the MEP pathway, however, are essential for *E. coli* growth (Heuston et al., 2012), which makes development of a knockout mutant difficult. Therefore, the second option was chosen that is to inhibit the MEP pathway by the addition of the pathway inhibitor fosmidomycin (Zhang et al., 2011). Fosmidomycin is an antibiotic that inhibits 1-deoxy-D-xylulose 5-phosphate reductoisomerase (DXR) of the MEP pathway in native *E. coli*, and it ultimately blocks the only route to generate IPP and DMAPP. By adding fosmidomycin to the cultures of the screening platform strain, isoprenoids for *E. coli* growth could solely be derived from carbon flux through the heterologously expressed IPP-bypass MVA pathway in the presence of an adequate enzyme to convert IP to IPP. In nature, archaea have a unique isoprenoid pathway where IP is phosphorylated to IPP by IP kinase (Chen and Poulter, 2010). In the screening platform, archaeal IP kinases (IPK) were heterologously expressed to generate IPP via phosphorylation of IP produced from the IPP-bypass MVA pathway (FIG. 1B).

Fosmidomycin sensitivity was tested by introducing various amounts of fosmidomycin into DH1, BW25113 and BL21, three *E. coli* strains commonly used for microbial metabolic engineering. DH1 was significantly more susceptible than the other two strains to fosmidomycin, as it was the only strain that had no growth on 10 µM fosmidomycin. At higher concentrations of fosmidomycin, cell death was accelerated in DH1, supported by a fast reduction in optical density (OD) at 600 nm after approximately two hours of exposure to fosmidomycin. On the other hand, both BL21 and BW25113 continued to grow for approximately four hours when exposed to equivalent fosmidomycin levels. Therefore, DH1 was selected as a host strain to screen PMD mutants for improved MVAP decarboxylation activity and subsequent isopentenol production in this study.

Subsequently it was confirmed that growth inhibited by fosmidomycin resumed in DH1 by allowing IPP production from IP, which is generated via the IPP-bypass MVA pathway (FIG. 1B). Three kinases with previously reported activity towards IPIspE from *E. coli* (EcIPK) (Lange and Croteau, 1999) and two archaeal IP kinases (Funke et al., 2010) from *Methanothermobacter thermautotrophicus* (MtIPK) and *Thermoplasma acidophilum* (TaIPK)—were heterologously expressed (JBEI-15323, JBEI-15642 and JBEI-15350, respectively) in DH1 together with wild type PMDsc (JBEI-15645). Expression of two archaeal IP kinases, MtIPK, and TaIPK, enabled growth recovery of the DH1 strains under fosmidomycin selection pressure, suggesting higher kinase activity of MtIPK and TaIPK compared to that of EcIPK (FIG. 2A). Between two strains expressing the archaeal IPKs, the strain that expressed the MtIPK showed a shorter lag phase (2 hours vs 3-4 hours) regardless of expression level of PMDsc (10 or 100 nM anhydrotetracycline (aTc)) (Lee et al., 2011), suggesting that MtIPK provides better sensitivity to the screening platform. On the other hand, when an inactive mutant, PMDsc-S208E (Kang et al., 2016), was co-expressed (JBEI-15647), none of three IPK-expressing DH1 strains (SP4, SP5 and SP6) could grow. This result supports the screening platform design hypothesis, which implies that cellular growth is solely dependent upon decarboxylation of MVAP within the heterologously expressed IPP-bypass pathway. In addition, resistance to fosmidomycin, which could be developed by adaptive mutations (Martinez and Baquero, 2000), was not observed under the condition of the screening platform and during growth recovery experiments.

After optimizing the screening conditions where *E. coli* DH1 can survive only from IPP produced from IP generated solely from the MVA pathway, it was tested whether the growth rate of *E. coli* DH1 correlated with the relative enzyme activity of PMDsc on MVAP. The kinetics of six PMDsc variants (K22M, R74H, I145F, T209D, S155E and S208E) revealed that two mutants, K22M and R74H, were shown to either decrease or increase isopentenol titers, respectively, in accordance with altering $k_{cat}$ or $k_{cat}/K_M$ of PMDsc for MVAP (Kang et al., 2016). Therefore, the growth rates of K22M and R74H mutants were determined along with positive (WT PMDsc) and negative (inactive S208E mutant) controls under the screening conditions.

Figure 2B:
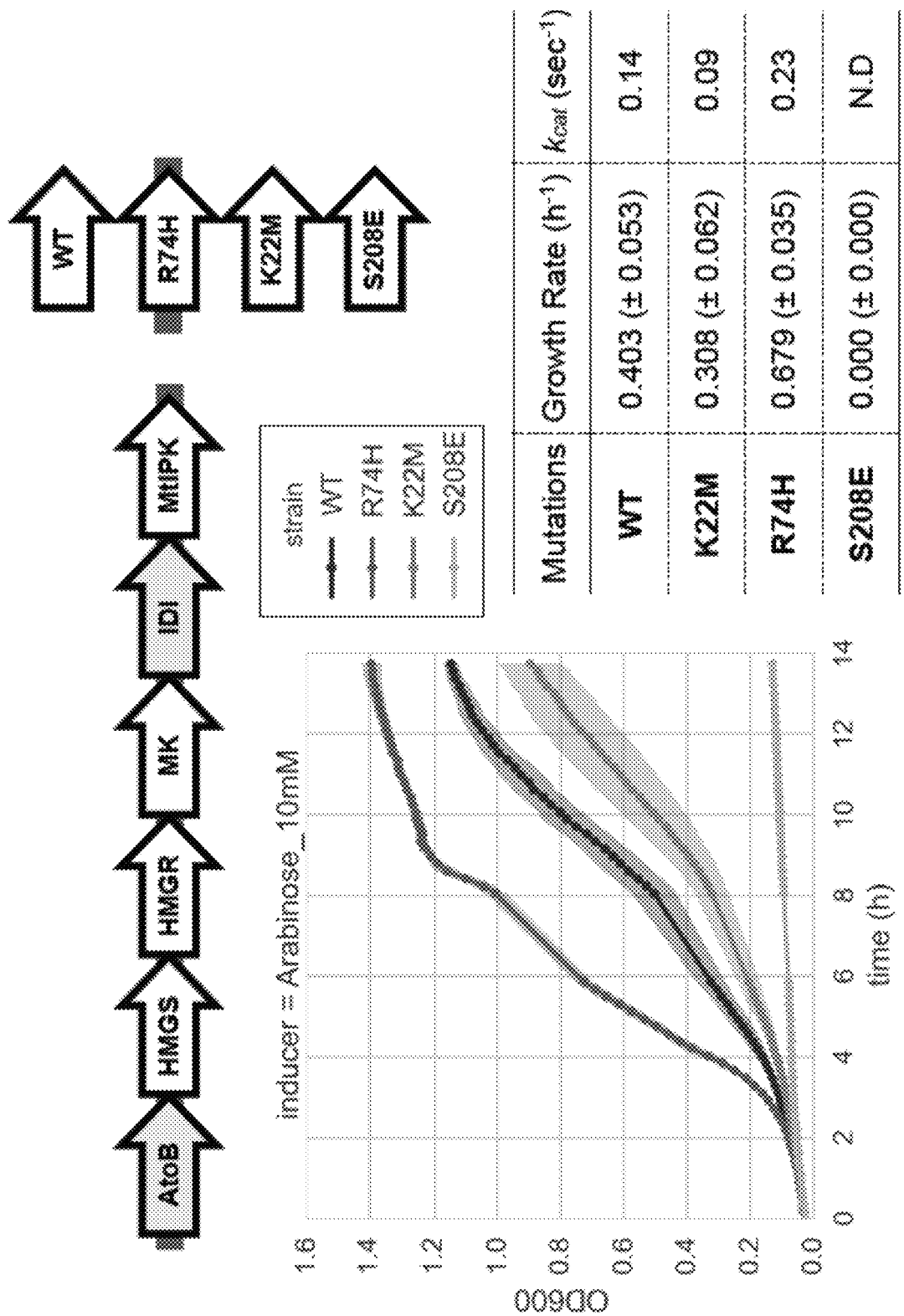

As shown in FIG. 2B, the growth rates of these four strains varied depending on the MVAP decarboxylation activity and expression level of PMDsc. When these enzyme variants were expressed at lower inducer concentrations (10 nM aTc) or with low copy number plasmids (FIG. 2B), the growth rates of the DH1 strains harboring the corresponding screening plasmids were dependent on the MVAP-decarboxylation activity of PMDsc variants. Strains with R74H grew faster than the strain with WT PMDsc, while strain harboring the K22M mutant exhibited decreased growth rates relative to wild type. In addition, it was confirmed that a strain harboring wild type PMDsc grew at different rates when the PMDsc was expressed at different inducer concentrations (data not shown). However, when protein expression levels of PMD variants were increased by using 10-fold higher inducer concentrations (100 nM aTc), all *E. coli* DH1 with active PMDsc variants K22M, R74H, and WT showed similar growth rates (0.83±0.01 hr$^{1}$). This result suggests that expression of PMD needs to be tightly regulated to keep the sensitivity of the screening platform such that the selection pressure would reflect the relative catalytic activity of PMDsc mutants.

Subsequently, the sensitivity and selectivity of the screening platform was further verified by competitive growth among the three DH1 strains containing PMDsc WT, K22M and R74H. A mixed seed culture was prepared by combining an equal starting amount of each of the three strains and incubated overnight. The mixed population was diluted and regrown in fresh medium supplemented with 10 µM fosmidomycin. Sequencing data revealed that DH1 expressing PMDsc-R74H was the dominant strain present after several dilutions of the mixed culture. Again, this result confirmed that the screening platform selects for PMDsc mutants with increased activity among a mixed population of strains via growth competition.

Screening of Saturation Mutagenesis Libraries

After testing selectivity of the screening platform, two sets of libraries of PMDsc mutants were constructed and tested: one library was constructed by codon saturation mutagenesis on seven rationally targeted residues and the other was constructed by error-prone PCR to generate random mutations in PMDsc.

Figure 3A:
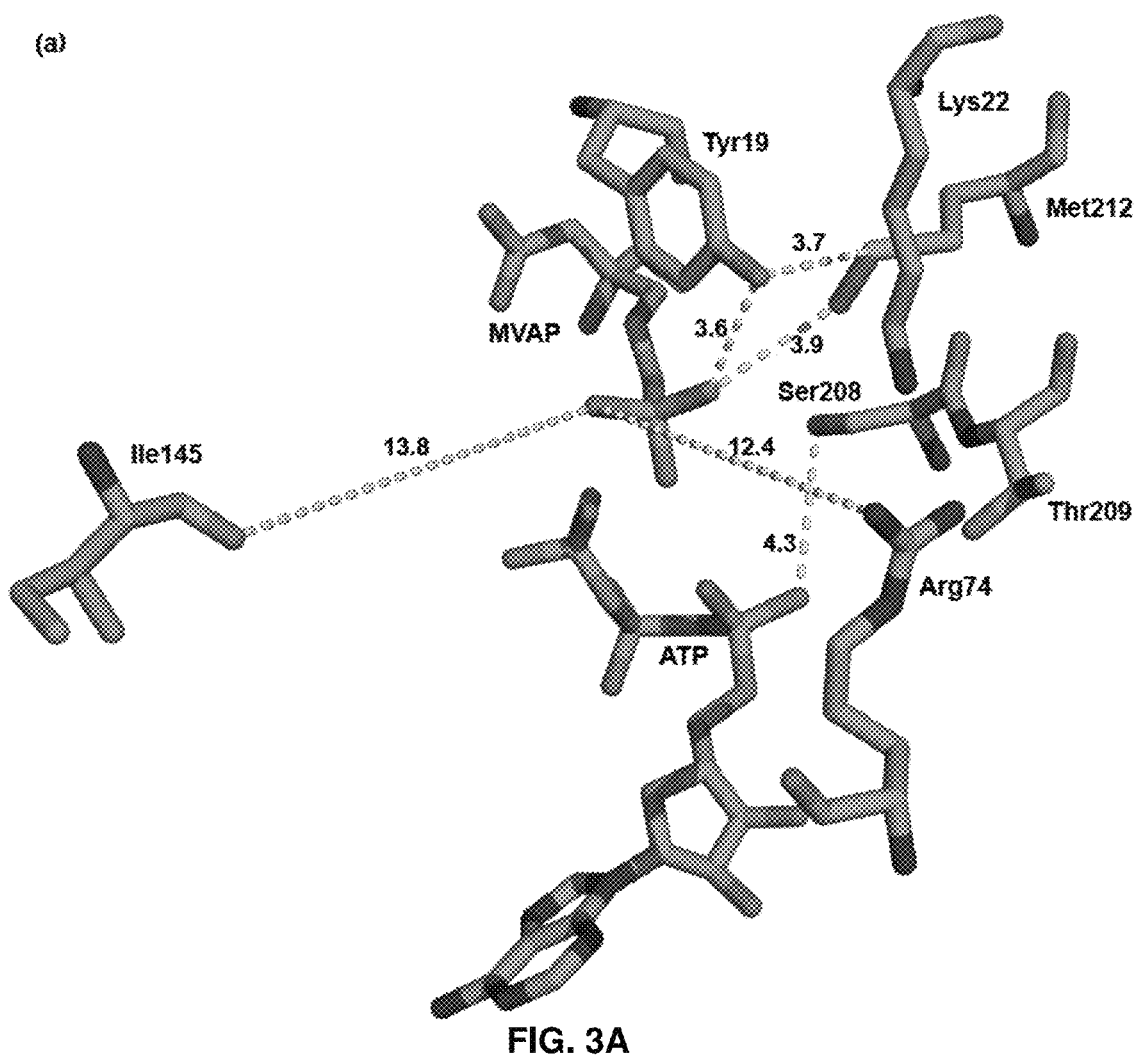
FIG. 3. Screening of targeted saturation mutagenesis library (A) Residues for saturation mutagenesis including Tyr19, Lys22, Arg74, Ser208, Thr209 and Met212; MVAP, mevalonate phosphate; ATP, adenosine triphosphate. (B-C) Isopentenol production titers of single mutants (B) and double mutants (C) including R74H, which was previously identified. Light grey bars are titers measured 24 hours after induction and dark grey bars are titers after 48 hours of induction. The reference line is the titer of wild type PMDsc (WT) 48 hours after induction. Titers were calculated with three biological replicates (n=3).

Five residues (Tyr19, Lys22, Ser208, Thr209 and Met212) were selected for codon saturation mutagenesis (FIG. 3A). Although a crystal structure of PMDsc with a substrate analog is not available, structural alignment of PMDsc (1F14) (Bonanno et al., 2001) with a homologous PMD isolated from *Staphylococcus epidermidis* (PMDse) revealed several parallels between their active sites (Barta et al., 2011). Tyr19 and Lys22 in PMDsc correspond to Tyr18 and Lys21 in PMDse, and these homologous residues most likely interact with the pyrophosphate group of the native substrate, MVAPP. The hydroxyl side chain of Ser208 in PMDsc (Ser192 in PMDse) is appropriately positioned to form hydrogen bonds with the a-phosphate moieties of bound ATP and MVAPP in the ternary complex model of PMDse (Barta et al., 2012). Thr209 and Met212 of PMDsc, which correspond to Arg193 and Met196 in PMDse, provide second-sphere structural support for the residues directly interacting with active site substrates (FIG. 3A). Two additional residues, Arg74 and Ile145, were also selected based on the previous kinetic data implicating their potential to increase the decarboxylase activity of PMDsc (Kang et al., 2016). R74H and I145F increased $k_{cat}$ for decarboxylation of multiple substrates in PMDsc, including 3-hydroxy-3-methylbutyrate (Gogerty and Bobik, 2010) and MVAP (Kang et al., 2016).

Figure 3B:
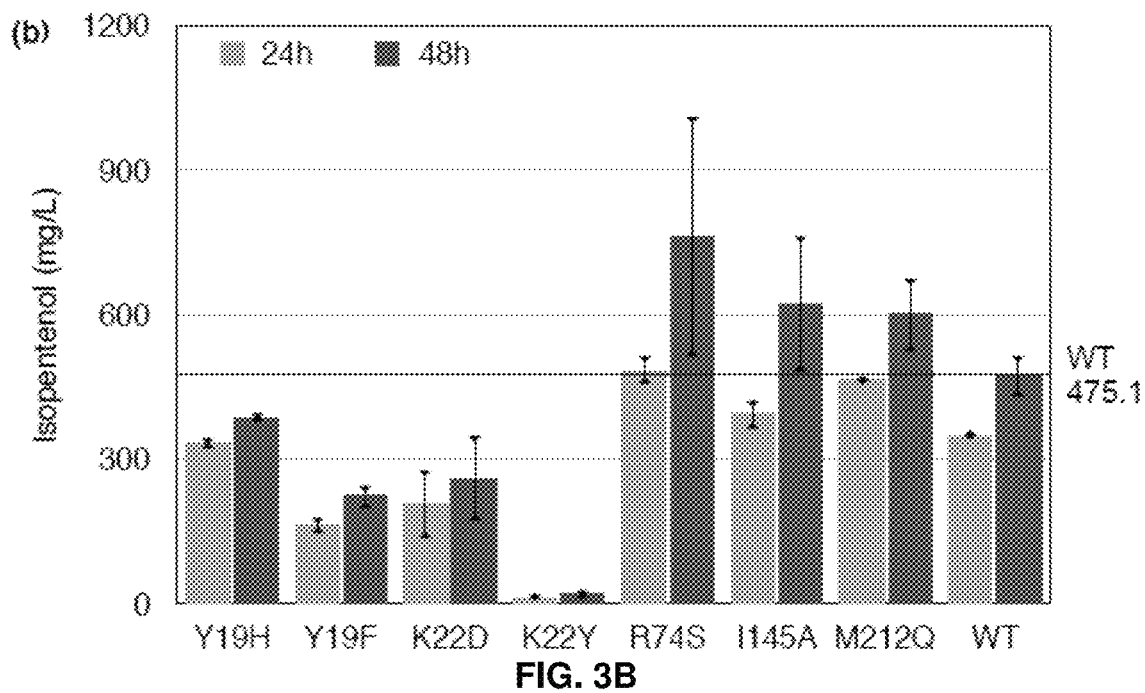
Figure 3C:
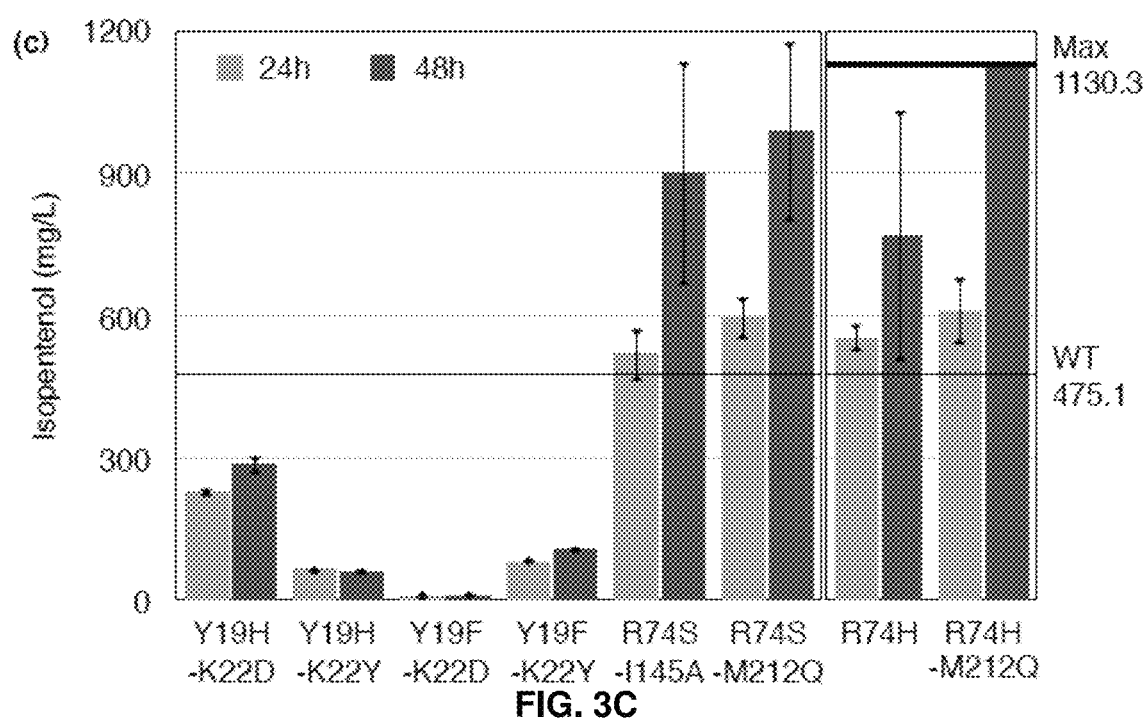
Figure 4A:
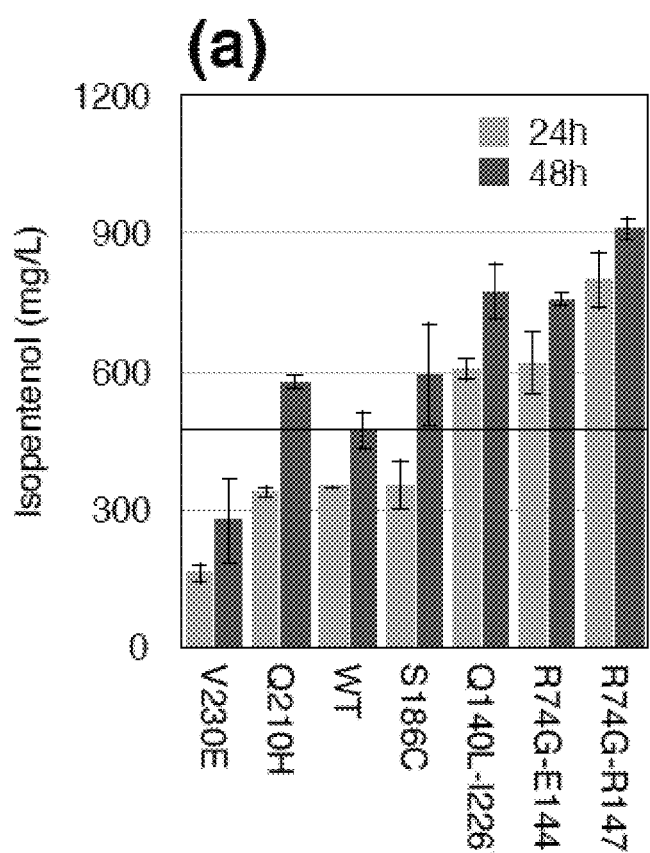
FIG. 4. Screening of random mutagenesis library. (A) Isopentenol titers produced from DH1 strains containing JBEI-9310 and various PMDsc mutants concurrently identified from random mutagenesis libraries and (B) single mutant of the identified residue. (C) Triple mutants were generated based on promising residues identified in this study and a previous study (Kang et al., 2016). The reference line at 475.1 mg/L is isopentenol titer of wild type PMDsc (WT) after 48 hours induction and thicker reference line at 1079.1 mg/L is maximum isopentenol titer of the mutant, R74H-M212Q-R147K after 48 hours of induction. Light grey bars are titers after 24 hours induction and dark grey bars are titers after 48 hours of induction. Titers were calculated with three biological replicates (n=3).
Figure 4B:
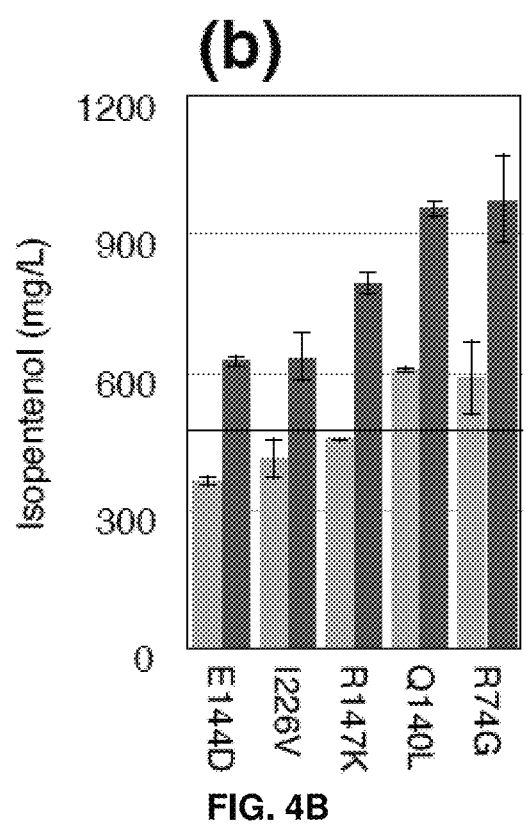
Figure 4C:
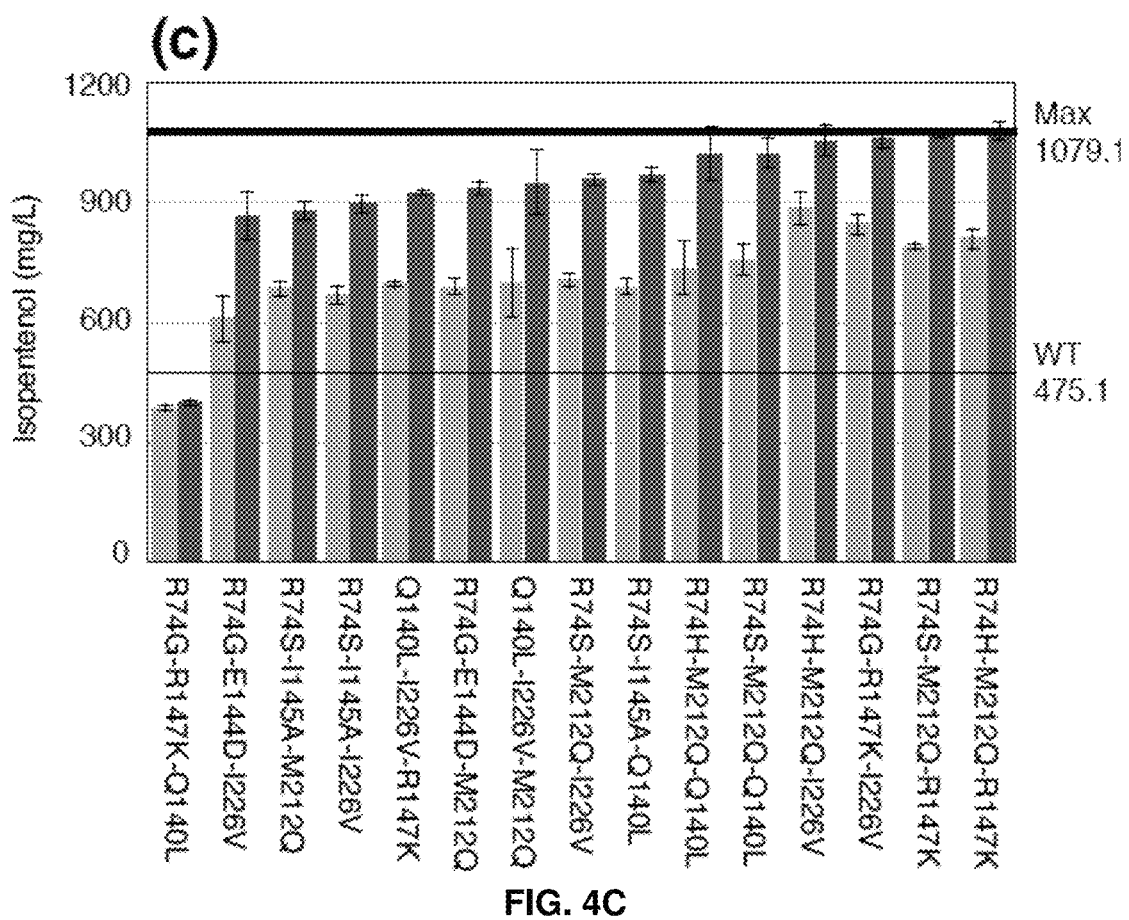

Screening of the codon saturation mutagenesis libraries resulted in a dominant amino acid for each residue of Arg74, Ile145, Ser208 and Met212, but the selective effects on the other three residues, Tyr19, Lys22 and Thr209 were not clear and the sequencing result still showed mixed signals of all nucleotides. Three of the four dominant residues, Arg74, Ile145 and Met212, were substituted to serine, alanine and methionine respectively, and it was found that these three mutations (M212Q, R74S, and I145A) significantly improved isopentenol production via the IPP-bypass MVA pathway (FIG. 3B). DH1 strains expressing these three mutants significantly increased isopentenol production relative to WT (475.1 mg/L), with titers ranging from 600-800 mg/L. Such improvement is in line with increases found in R74H (770.3 mg/L) from a previous study (Kang et al., 2016). Interestingly, combinations of select double mutants, R74S-I145A, R74S-M212Q, and R74H-M212Q, significantly increased isopentenol titers by up to 2.4-fold relative to wild type: strains containing these double mutants further improved titers from 900-1130 mg/L 48 hours after induction with IPTG (FIGS. 4A to 4C). Selection of seven codon saturation mutagenesis libraries successfully demonstrated that the screening platform could identify PMDsc mutants that have potentially higher activity towards MVAP and increased isopentenol titers from the IPP-bypass MVA pathway.

In addition to finding mutated residues improving isopentenol production in the IPP-bypass pathway, it also confirmed that the screening platform effectively inhibits the growth of the strain with inactive PMD variants. Alignment-based structural predictions mapping PMDsc to a crystal structure of PMDse suggest that Ser208 forms essential hydrogen bonds with both the α-phosphate of ATP and the α-phosphate of MVAPP. It was shown that S208E is inactive toward MVAP (Kang et al., 2016), and another study reported that S208A compromised the structural stability of the PMDsc, resulting in protein precipitation (Krepkiy and Miziorko, 2005). Therefore, viable isopentenol-producing strains retaining the wild-type serine at residue 208 in PMDsc ensured the selection specificity of the screening platform for active PMD sequences. In addition to the S208E mutant, another inactive mutant (S155E) of PMD was tested as the second negative control and confirmed the impaired growth from the strain with S155E mutant (data not shown). This further supported the wild type selection result of S208 in the saturation mutagenesis library. Hence, strain selection is based solely on the enhancement of carbon flux through the IPP-bypass pathway facilitated by PMDsc activity toward the nonnative MVAP under the screening conditions.

In contrast, Thr209 could be substituted with any amino acid residue, suggesting that there was much less selection pressure on this residue within this screening platform. Thr209 of PMDsc is a structurally parallel residue to Arg193 of PMDse, which has been suggested to stabilize the β-phosphate of MVAPP (Barta et al., 2012). Although it was initially hypothesized that this residue might be critical to determine substrate promiscuity, it seems that the decarboxylation activity of PMDsc for MVAP was not significantly affected by alterations at residue 209. In accordance with this observation, it was shown that T209D did not significantly change the isopentenol titer in *E. coli* (Kang et al., 2016).

Screening of Random Mutagenesis Libraries

Since the size of the saturation mutagenesis libraries was relatively small (7×21=147 designs), libraries of randomly mutated PMDsc sequences were prepared by error-prone PCR (McCullum et al., 2010) to contain low-, mid- and high-mutation rates per coding sequence. The DH1 strains carrying JBEI-15350 and plasmids libraries of randomly mutated PMDsc were serially diluted into fresh medium containing fosmidomycin to enrich fast-growing strains until the growth rate did not significantly vary among all libraries. In total, there were three rounds of dilutions, but the exposure period of each library to fosmidomycin before the next round of dilution varied depending on the rate of growth recovery. Given the higher heterogeneity of initial libraries, the first dilution significantly extended the lag phase during growth. Thus, all surviving variants after the first selection were rescued overnight in fresh EZ-rich medium without fosmidomycin before the second dilution. At the end of the third dilution, all libraries exhibited similar growth rates (0.72±0.10 h$^{-1}$), which were higher than the average growth rate of the second round (0.49±0.11 h$^{-1}$) and comparable to that of R74H (0.68±0.04 h$^{-1}$). Sequencing of the amplified PMD sequences revealed that two-thirds of tested libraries were dominated by select PMDsc residues (Table 1), while the remaining mutants were enriched with the wild type PMDsc. Excluding redundant mutations, six unique PMDsc variants were cloned into pTrc99a vector, which were in turn co-transformed with JBEI-9310 into DH1 for isopentenol production via the IPP-bypass pathway. Most isopentenol producing strains with respective PMDsc mutants produced isopentenol at higher titers relative to wild type PMDsc except V230E. The highest 48-hour post-induction titers were obtained by the strains with three double mutants, R74G-R147K, Q140L-I226V, and R74G-E144D (FIGS. 4A to 4C), whose titers after 48 hours were 1.9-fold, 1.6-fold, and 1.6-fold higher than the strain with wild type PMDsc, respectively. However, not all selected mutations were cooperative for isopentenol production. R74G and Q140L produced isopentenol at levels similar to or better than those selected from the randomly mutated libraries, R74G-R147K, Q140L-I226V and R74G-E144D mutants.

TABLE 1

Mutated residues found in 15 replicates of random mutagenesis libraries. All mutations were confirmed by sequencing, and three libraries (L8, L9, L15) included silent mutations. Number of silent mutations refers to number of mutated nucleotides without altering wild type amino acids.

| ID | Mutated Residues | Number of silent mutations |
|---|---|---|
| L1 | Q210H | |
| L2 | R74G, R147K | |
| L3 | Wild type | |
| L4 | Wild type | |
| L5 | V230E | |
| L6 | Q210H | |
| L7 | S186C | |
| L8 | Q140L, I226V | 3 |
| L9 | R74G, E144D | 3 |
| L10 | Wild type | |
| L11 | Wild type | |
| L12 | Q210H | |
| L13 | Q210H | |
| L14 | Q210H | |
| L15 | R74G, E144D | 4 |

Correlating Screening Properties to PMD Catalytic Activity

Figure 6:
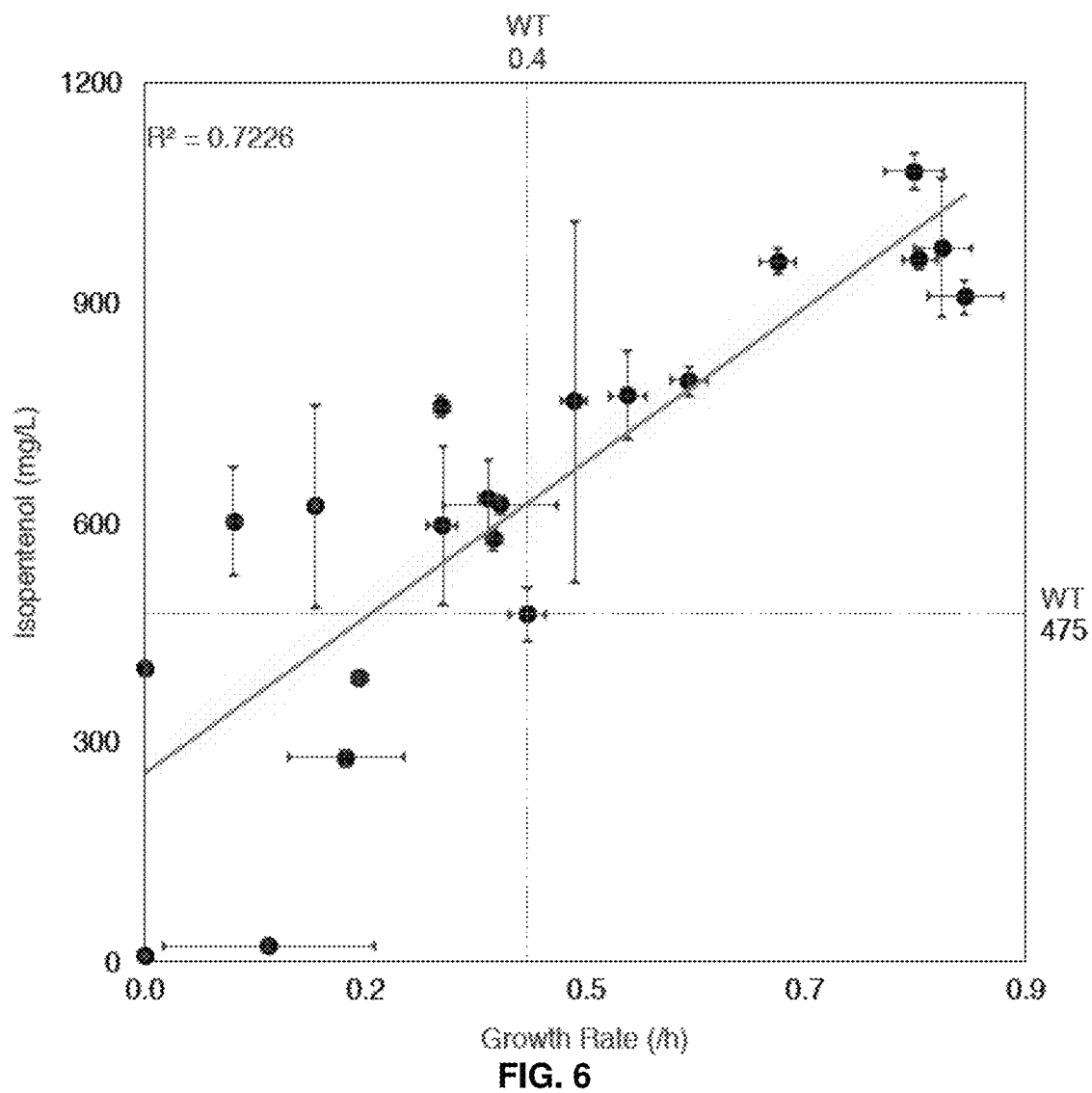
FIG. 6. Isopentenol titers and growth rates of 21 mutants (filled circles) with standard deviation of three biological replicates. Two reference lines (dotted) are wild type's growth rate (0.4) and isopentenol titer (475 mg/L). $R^2$ and the trend line (solid) were generated by linear regression.

The rationale behind the screening platform posits that in vivo MVAP-decarboxylation activity of PMD in DH1 correlates with the cellular growth rate under conditions where the endogenous MEP pathway is inhibited by fosmidomycin (FIG. 1B). This hypothesis assumes that the IPP production rate is limited by MVAP-decarboxylation by PMD (FIG. 1A). Isoprenoids are essential for E. coli growth, and therefore, in vivo MVAP-decarboxylation activity, which is determined by actual turnover rate of MVAP to IP in vivo, would determine the growth rate of a host strain, where PMD variants with different MVAP-decarboxylation activity are expressed in the screening platform (FIG. 1B). To further support this hypothesis, the growth rate for twenty mutants identified in this study was determined under the conditions implemented for mutant screening. The 20 mutants selected for this analysis were representative of all strains producing isopentenol via the IPP-bypass route, ranging from 22±8 mg/L (K22Y) to 1,080±30 mg/L (R74H-R147K-M212Q) (Table 2). As seen in FIG. 6, a scatter plot relating cellular growth rates to isopentenol titers shows a positive linear correlation with $R^2$=0.72, further corroborating that MVAP decarboxylation is indeed the rate-limiting step in the engineered IPP-bypass pathway. Given that the number of mutants identified in the screening platform is only 20, a rather low $R^2$ value was inevitably obtained. However, it should be noted that the correlation between growth rate and isopentenol titers are much better for high-producers (8 variants at right-top corner), which have higher titers and growth rates than WT (475.1 mg/L and 0.4 h$^{-1}$, respectively). Although the wider variation in growth rates was observed for poorly producing strains (e.g. two variants at left-bottom corner), it is likely that inactive and less active mutants are more subject to a growth-inhibited phenotype than for more active mutant primed for growth. On the other hand, it was noticed that several mutants, particularly with R74S, showed wider variation in isopentenol titers, possibly due to colony-to-colony variation often observed in over-producing strains. However, these variations found in growth rates and titers do not compromise the validity of the screen design, which demonstrates its selectivity for high-producers over low-producers.

TABLE 2

Enzyme kinetics ($k_{cat}$, $K_M$ and $k_{cat}/K_M$), growth rates (hr$^{-1}$) and isopentenol titers (at 48 hr, mg/L) of PMDsc mutants.

| Mutant | $k_{cat}$, sec$^{-1}$ | $K_M$, mM | $k_{cat}/K_M$, mM$^{-1}$ sec$^{-1}$ | Growth rate, hr$^{-1}$ | 48 hr Titer, mg/L |
|---|---|---|---|---|---|
| WT | 0.15 (0.01) | 2.3 (0.2) | 0.066 (0.007) | 0.39 (0.02) | 475 (40) |
| Y19H | 0.27 (0.01) | 0.35 (0.02) | 0.78 (0.06) | 0.22 (0.01) | 388 (9) |
| K22Y | 0.09 (0.01) | 1.3 (0.3) | 0.12 (0.03) | 0.13 (0.11) | 22 (8) |
| R74G | 0.14 (0.02) | 3.4 (1.0) | 0.04 (0.01) | 0.81 (0.03) | 975 (96) |
| R74H | 0.33 (0.03) | 0.75 (0.05) | 0.44 (0.05) | 0.68 (0.04) | 770 (263) |
| I145A | 0.029 (0.004) | 2 (1) | 0.01 (0.01) | 0.17 (0.00) | 623 (140) |
| R147K | 0.149 (0.006) | 0.5 (0.1) | 0.32 (.09) | 0.56 (0.02) | 793 (22) |
| S186C | 0.07 (0.01) | 0.8 (0.2) | 0.08 (0.02) | 0.30 (0.02) | 596 (110) |
| M212Q | 0.35 (0.02) | 0.7 (0.2) | 0.5 (0.1) | 0.09 (0.01) | 601 (76) |
| I226V | 0.16 (0.01) | 0.34 (0.06) | 0.46 (.09) | 0.35 (0.01) | 633 (53) |
| V230E | 0.07 (0.01) | 0.8 (0.2) | 0.08 (0.02) | 0.21 (0.18) | 278 (91) |
| R74G-R147K | 0.22 (0.01) | 0.53 (0.05) | 0.42 (0.05) | 0.84 (0.04) | 909 (25) |

TABLE 2-continued

Enzyme kinetics ($k_{cat}$, $K_M$ and $k_{cat}/K_M$), growth rates ($hr^{-1}$) and isopentenol titers (at 48 hr, mg/L) of PMDsc mutants.

| Mutant | $k_{cat}$, $sec^{-1}$ | $K_M$, mM | $k_{cat}/K_M$, $mM^{-1} sec^{-1}$ | Growth rate, $hr^{-1}$ | 48 hr Titer, mg/L |
|---|---|---|---|---|---|
| R74H-R147K-M212Q | 0.16 (0.02) | 0.4 (0.2) | 0.4 (0.1) | 0.79 (0.03) | 1079 (27) |
| R74G-R147K-M212Q | 0.22 (0.04) | 0.5 (0.1) | 0.5 (0.2) | N.D. | 8 (1) |
| R74G-R147K-Q140L | 0.06 (0.01) | 2 (1) | 0.03 (0.02) | N.D. | 401 (10) |

N.D.: not detected.
The numbers in brackets are either standard errors (kinetics) or standard deviation (growth rates and titers).

Potential Secondary Structure Effects of the Mutated Residues

Figure 5:
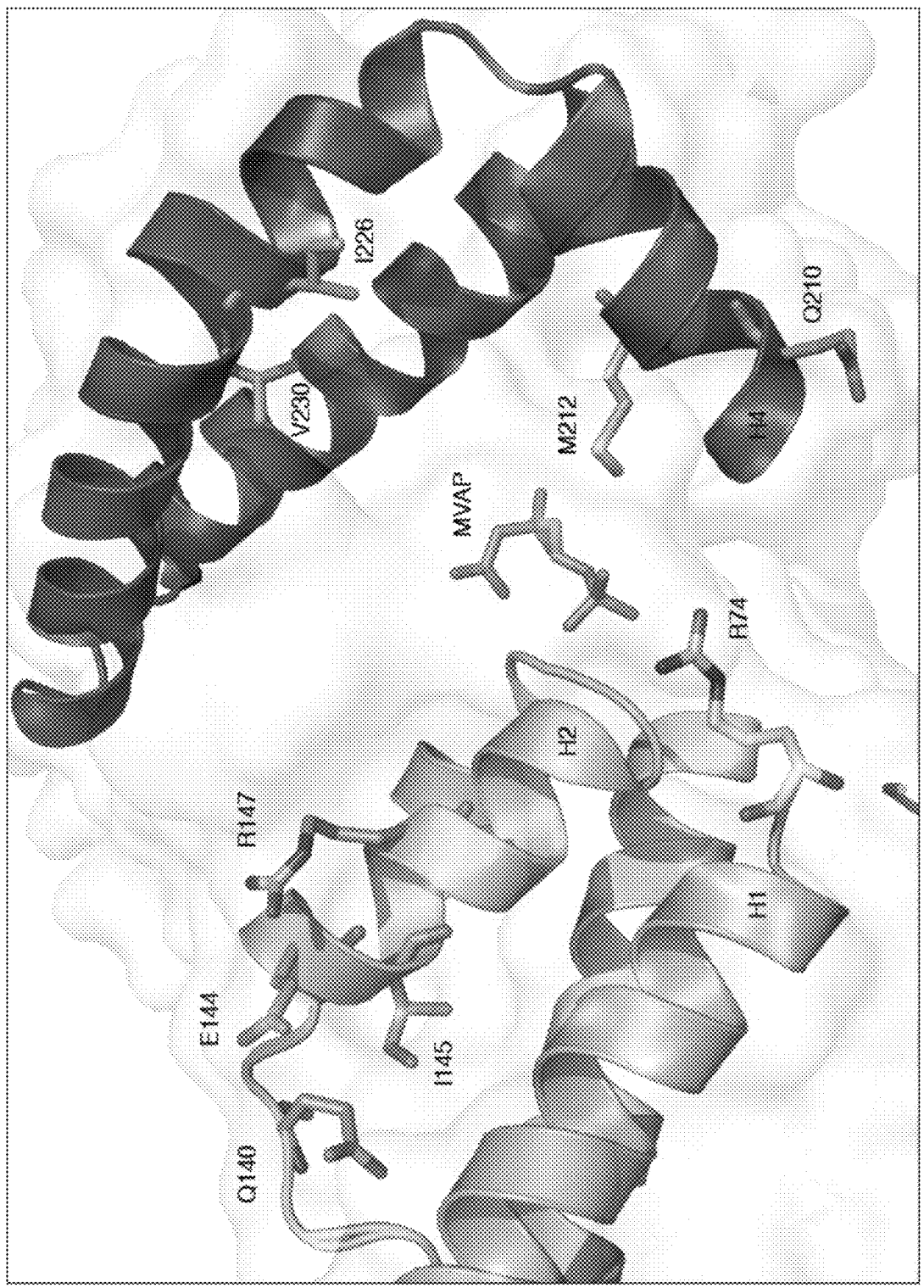
FIG. 5. A cartoon representation of PMDsc structure with the 9 identified residues in this study. Four helix secondary structures are highlight with the substrate, MVAP: α-helix 1 (H1, skyblue), α-helix 2 (H2, mustard); α-helix 4 and α-helix 5 (H4-H5, purple).

It is noteworthy that this study identified important residues distal to the active site that enhanced isopentenol production, implicating the possibility that interactions between a-helices could affect the activity of PMDsc for MVAP decarboxylation (FIG. 5). The screening platform revealed that two of these helical residues, Arg74 and Ile145, could tolerate several substitutions to facilitate enhanced isopentenol production. In addition to the initially reported mutant (R74H), it was found that smaller glycine and serine substitutions were beneficial at position 74, showing that protonated side chains in this locale are not necessary for improving enzymatic activity. While I145F was shown to modestly improve enzyme activity in a previous study (Kang et al 2015), the emergence of I145A from the screening platform showed that packing properties around position 145 can affect the PMDsc activity toward nonnative substrates. However, it is not clear how these distal residues increase activity of PMD toward MVAP. Since both Arg74 and Ile145 residues are quite far from the active site (FIG. 3A), substitutions at these locales could result in altered interactions between neighboring α-helices. These altered packing modes might cause alternative kinetic consequences rather than directly impacting substrate binding. Particularly, Arg74 appears to shield the active site from bulk solvent by interacting with a loop containing several substrate binding domain residues (17-33) proposed to be critical for catalysis.

The kinetic impact arising from Ile145 is much less clear, as this residue is more than 15 Å away from the cofactor moiety. Interestingly, it was found three additional single mutants (Q140L, E144D, R147K) that reside near Ile145, and all of them resulted in increased isopentenol production titers (FIGS. 4A to 4C). Gln140, Glu144, Arg147, and Ile145, are all located on a-helix 2 (H2) (FIG. 5), and small conformational changes made by these mutants might affect the two serine residues (Ser120 and Ser121) at C-terminal end of H2. These serine residues provide essential hydrogen bonds that stabilize MVAP with ATP. In addition to these four residues, three more distant residues, Gln210, Ile226, and Val230, located on α-helix 4 (H4) (FIG. 5), were also identified which could alter substrate binding modes for MVAP.

Since it was found a positive correlation between isopentenol titers using mutant PMDs and their respective growth rates in the screening platform, it was initially expected that a direct correlation between kinetic parameters ($k_{cat}$ and $k_{cat}/K_M$) of mutant PMDs and either isopentenol titers or growth rates would be observed. However, there was no significant correlation between kinetic activity of mutants and isopentenol and/or cellular growth rates. The kinetics of fourteen PMDsc variants for enzymatic decarboxylation (Table 2) showed that many mutants significantly increased $k_{cat}/K_M$ for MVAP, which includes kinetic steps associated with substrate and cofactor binding. However, increasing $k_{cat}/K_M$ does not improve growth rates or isopentenol titers.

The most striking data for $k_{cat}/K_M$ arise from the Y19H and M212Q mutants, which are proposed to interact with the phosphate moieties of the native MVAPP substrate (FIG. 3A).

Like other diphosphate decarboxylases, the conserved P-loop motif (Barta et al., 2012; Saraste et al., 1990) closes upon ATP binding, which then coordinates substrate and cofactor for catalysis (Barta et al., 2012). Since MVAP lacks the β-phosphate group, the active site needs to be more compact to prevent packing defects within the active site. In the structural alignment model, the Met212 residue is less than 4 Å from the predicted binding site of the a-phosphate moiety in MVAP (FIG. 3A). Therefore, its mutation to glutamine (M212Q) could provide additional hydrogen-bonding interactions with this phosphate moiety to help stabilize MVAP, thereby increasing $k_{cat}/K_M$ (0.5±0.1 $mM^{-1}$ $s^{-1}$) (Table 2).

Similarly, it was hypothesized that mutations at residue 19 might improve stabilization of α-phosphate based on the previous computational study (Weerasinghe and Samantha Dassanayake, 2010), and therefore it was aimed to find a better-positioned residue that might interact with the α-phosphate of MVAP. Indeed, Y19H increased $k_{cat}/K_M$ of PMDsc about 10-fold (0.78±0.06 $mM^{-1}$ $s^{-1}$) (Table 2) compared to that of wild type, exhibiting the largest increase of $k_{cat}/K_M$ relative to wild type. Although both M212Q and Y19H increased $k_{cat}/K_M$ of PMDsc, interestingly only M212Q could significantly increase isopentenol titer, while Y19H rather significantly decreased isopentenol titers (Table 2).

Analysis of all characterized mutants revealed that there was no significant correlation between $k_{cat}$ (or $k_{cat}/K_M$) and the cellular growth rate or the isopentenol titer. For example, the activity of a triple mutant, R74G-R147K-M212Q ($k_{cat}/K_M$=0.5±0.2 $mM^{-1}$ $s^{-1}$), was comparable to that of R74H-R147K-M212Q ($k_{cat}/K_M$=0.4±0.1 $mM^{-1}$ $s^{-1}$), but its isopentenol titer after 48 hours (8±1 mg/L) was 135-fold less than that of R74H-R147K-M212Q (1,079 mg/L). Similarly, R74G's $k_{cat}/K_M$ is comparable to WT's $k_{cat}/K_M$, but the strain expressing R74G produced significantly higher amount of isopentenol compared to that of WT (Table 2).

Effect of MVAP Inhibition on PMDsc Mutants for Decarboxylation

The correlation analysis between isopentenol titers and kinetics of the mutants suggested that there must be other factors that determine the actual decarboxylation activity in vivo under isopentenol production conditions or growth-based selection conditions. In a previous study, it was found that the E. coli production strain containing the IPP-bypass MVA pathway and wild type PMD accumulated significantly higher concentration of MVAP compared to that of the original pathway within 5 hours after induction (Kang et al., 2016). Assuming in vivo MVAP concentration is well above the $K_M$ for wild type PMDsc ($K_M$(MVAP)=2.3±0.2 mM), it was hypothesized that noncompetitive substrate inhibition might affect the in vivo decarboxylation activity. At such high concentrations of MVAP in vivo, the rate enhancements on $k_{cat}/K_M$ observed in vitro for select mutants would not necessarily be observed. Considering importance of the native mevalonate pathways for isoprenoid metabolism, the activity of PMDsc might be tightly regulated by MVAP concentrations in vivo since a low $K_I$ would significantly decrease the rate of decarboxylation as excess MVAP accumulates. This directs MVAP flux through the phosphomevalonate kinase (PMK) enzyme to generate MVAPP, the preferred native substrate for PMDsc, rather than increasing futile decarboxylation of MVAP to IP.

Figure 7:
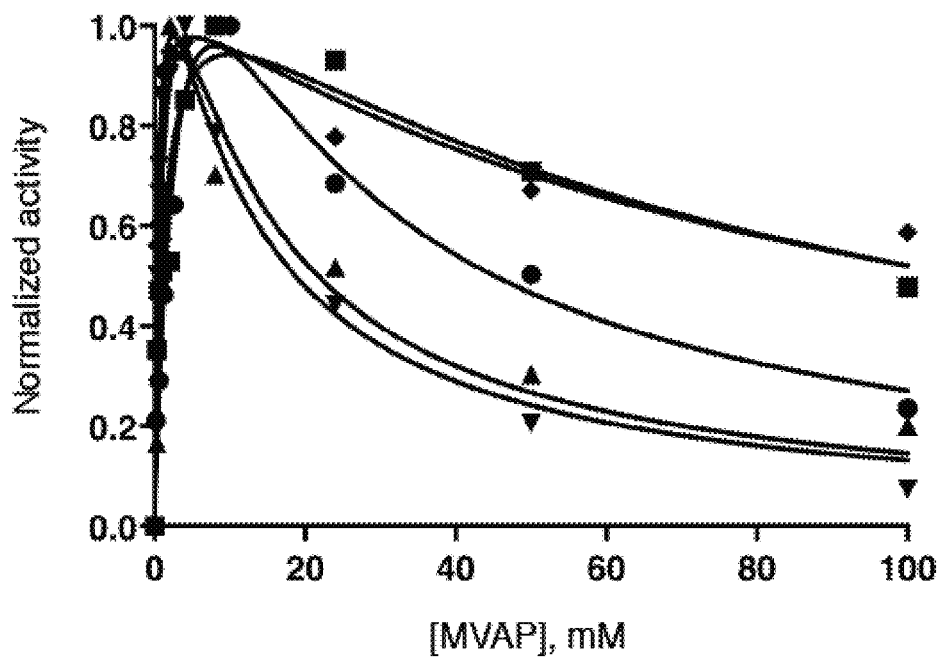
FIG. 7. Determination of the noncompetitive substrate inhibition constant, $K_I$, for select PMDsc mutants: WT (circles); R74G (squares); V230E (upward triangles); R74G: R147K:M212Q (downward triangles); R74H:R147K: M212Q (diamonds). All activities reported are normalized relative to each mutant's $k_{cat}$ derived from fits to the noncompetitive substrate inhibition expression. Parameters were derived from three technical replicates (n=3).

WT and four mutants, R74G, V230E, R74G-R147K-M212Q and R74H-R147K-M212Q, were specifically selected for substrate inhibition study, where activity was measured in wide range of MVAP concentrations up to 100 mM (FIG. 7). These variants representatively spanned a wide range of isopentenol titers (8-1,080 mg/L), and their substrate inhibition behavior was characterized by determining each mutant's $K_I$ (Table 3). Interestingly, two higher isopentenol producing mutants (R74G and R74H-R147K-M212Q) exhibited significantly higher $K_I$'s (110 mM and 80 mM, respectively) than those with lower isopentenol producers (WT, 18 mM; V230E, 10 mM; and R74G-R147K-M212Q, 11 mM) (FIG. 7). A correlation emerged between growth rates (and/or titers) and PMD activity when an observed turnover number was calculated at 100 mM MVAP using the analytical expression for noncompetitive substrate inhibition, $k_{obs}$. This turnover number ($k_{obs}$) depends upon each mutant's $k_{cat}$, $K_M$, and $K_I$, yielding a more accurate assessment of the turnover conditions in vivo (Kang et al., 2016). The relationship between growth and $k_{obs}$ of these mutants suggests that the screening platform directly reports on the extent of substrate inhibition in PMDsc mutants (FIG. 7). This sensitivity of an in vivo screening platform to a mutant's $K_I$ modulation speaks to its power in analyzing the robustness of heterologously expressed mevalonate pathways within overexpressing bacterial strains.

growth of the organism (Packer and Liu, 2015). In this study, a growth-based screening platform to improve PMD decarboxylation activity toward MVAP for isopentenol production was designed. To achieve this goal, the growth rate of the E. coli DH1 was coupled to the decarboxylation rate of MVAP (FIG. 1B); the subsequent product formation of IP is ultimately converted to isopentenol via IPP-bypass MVA pathway (FIG. 1A). Codon saturation mutagenesis and random mutagenesis generated two separate enzyme mutant libraries, both of which were tested by this newly developed screening platform. This growth-based screening platform identified a new set of PMDsc mutants that significantly increased isopentenol production up to 1,130±5 mg/L. Correlation of growth rates and decarboxylation rates of identified PMD mutants confirmed the in vivo selectivity of the screening platform, and kinetics studies of the mutants suggested the robustness of this screening platform by providing biological context with respect to the target enzyme activity under relevant metabolite concentrations. Alteration of PMD and IPK expression levels coupled with tuning the inhibition strength of fosmidomycin provides the screening platform with more flexibility, potentially enabling further improvements of isopentenol production via the novel IPP-bypass pathway.

Materials and Methods

Development of the PMD Screening Platform

For the screening platform, a plasmid harboring 6 genes—AtoB, HMGR, HMGS, MK, Idi and a gene coding IP kinase (IPK)—was constructed by adding Idi and IPK to the plasmid (JBEI-9310) used for isopentenol production. AtoB and idi were native genes of E. coli while HMGR, HMGS, and MK were derived from S. cerevisiae. Two archaeal IP kinases from Methanothermobacter thermautotrophicus (MTH) and Thermoplasma acidophilum (THA) were amplified from two plasmids, pET15b-MTH and pET28b-THA, respectively (Funke et al., 2010), using primers IPKMTH-F-BglII, IPKMTH-R-XhoI, IPKTHA-F-BglII and IPKTHA-F-XhoI. A gene coding a potential IP kinase from E. coli (EcIPK) was amplified by using two primers EcIPK-BglII-F and EcIPK-XhoI-R. Wild type PMDsc and PMDsc mutants were cloned into a SC101-based plasmid under control of an araBAD promoter ($P_{BAD}$) or into a

TABLE 3

Analysis of Ki and $k_{obs}$ for select mutants.

|  | $k_{cat}$, sec$^{-1}$ | $K_M$, mM | $K_i$, mM | $k_{obs}$, sec$^{-1}$ | Growth rate, hr$^{-1}$ | 48 hr Titer, mg/L |
|---|---|---|---|---|---|---|
| WT | 0.15 | 2.3 | 18 | 0.02 (0.01) | 0.39 (0.02) | 475 (40) |
| R74G | 0.14 | 3.4 | 110 | 0.07 (0.04) | 0.81 (0.03) | 975 (96) |
| V230E | 0.07 | 0.8 | 10 | 0.006 (0.004) | 0.2 (0.2) | 278 (91) |
| R74G-R147K-M212Q | 0.22 | 0.5 | 11 | 0.022 (0.008) | N.D. | 8 (1) |
| R74H-R147K-M212Q | 0.16 | 0.43 | 80 | 0.07 (0.03) | 0.79 (0.03) | 1079 (27) |

N.D.: not detected.

Conclusion

Evaluation of enzyme libraries is often limited by the throughput of a screening method. In this regard, growth-based selection is powerful because it does not require extensive tests of an individual design, and designs with the desirable activity are enriched if the activity is essential for ColE1-based plasmid under control of a Tet promoter ($P_{Tet}$) (pBbE2a) (Lee et al., 2011). Mutant libraries were transformed in DH1 containing pBbA5c-MevTo-BBa1002-pTrc-MKco-EcIdi-MtIPK (JBEI-15350), and DH1 strains with libraries of PMDsc mutants were tested in the presence of fosmidomycin.

Cloning and Library Construction

Seven amino acid residues (Tyr19, Lys22, Arg74, Ile145, Ser208, Thr209, Met212) were selected for saturated mutagenesis. Tyr19, Lys22, Ser208, Thr209, and Met212 were chosen based on their vicinity to the β-phosphate group of MVAPP in a resolved crystal structure of PMDse (Barta et al., 2012) in a structural alignment of PMDsc to PMDse. Additionally, two distal residues, Arg74 and Ile145, have been shown to promote promiscuous decarboxylation activity of PMDsc toward non-native substrates (MVAP and 3-hydroxy-3-methylbutyrate (3-HMB) (Gogerty and Bobik, 2010; Kang et al., 2016). Amplified PCR products containing specific saturation mutagenesis were cloned to pBbS8a vectors.

Randomly mutated PMDsc sequences were generated by error-prone PCR (McCullum et al., 2010) using two primers, j5_00001_(PMDsc)_forward and j5_00002_(PMDsc)_reverse. The error-prone PCR buffer was supplemented with various concentrations of $MgCl_2$ and $MnCl_2$ to generate different mutation rates. Initially, 100 ng of JBEI-12052 was used as a template for PCR, and 1 µL Taq polymerase and 1 µL of 50 mM $MnCl_2$ (final 0.5 mM) were added just before the PCR runs. Every 5 cycles, PCR product was diluted 10-fold in fresh error-prone PCR buffer and additional 1 µL Taq polymerase and 1 µL 50 mM $MnCl_2$ (Final would be 0.5 mM) was added to 100 µL PCR reactions. To prepare low-mutation-rate libraries, a few PCR reactions were prepared with lower concentration of $MnCl_2$ and/or $MgCl_2$ with only 5 cycles. All PCR products were digested with DpnI to remove the template plasmids. Purified PCR products were assembled into pBbE2a by Gibson assembly.

Randomly mutated PMDsc sequences were grouped into three libraries according to their mutation rates, low (1-2 bases per coding sequence (CDS)), mid (3-4 bases per CDS) and high (more than 10 bases per CDS) mutation rates. These three libraries were transformed in the screening host strain DH1 and three colony-full plates were used for the screening. Number of colonies on each plate was estimated to around $10^3$-$10^4$.

Screening Procedures and Conditions

Saturation mutagenesis libraries of PMDsc cloned into a SC101-based plasmid under control of an araBAD promoter ($P_{BAD}$) were transformed into in E. coli DH1 strains harboring JBEI-15350. Cultures were suspended in EZ-Rich medium containing 1% glucose, 0.1 mM IPTG, 30 µg/mL chloramphenicol (Cm) and 100 µg/mL ampicillin (Amp), and incubated at 37° C. at 200 rpm overnight. These cultures were diluted to OD 0.3 in 500 µL EZ-rich medium containing 1% glucose, 0.1 mM IPTG, 50 µM fosmidomycin, and 10 mM arabinose. 500 µL cell cultures were prepared in 96 deep-well plates and incubated at 37° C. with a shaking speed of 700 rpm in a rotary shaking incubator (HT Infors Multitron; 44% humidity). After 16-18 hours of incubation (Day 2), the overnight cultures were diluted again to OD 0.1 in fresh 500 µL EZ-rich medium containing 1% glucose, 0.1 mM IPTG, 50 µM fosmidomycin and 10 mM arabinose. 500 µL cell cultures were prepared in 96 deep-well plates incubated at 37° C. and a shaking speed of 700 rpm in a rotary shaking incubator (HT Infors multitron; 700 rpm, 37° C., 44% humidity) for 8-16 hours. Next day (Day 3), the overnight cultures were diluted to initial OD of 0.05 in 200 µt EZ-rich medium containing 1% glucose, 0.1 mM IPTG, 50 µM fosmidomycin and 10 mM arabinose, and the optical density at 600 nm were obtained in the 96-well plates incubated at 37° C. at a shaking speed of 173 rpm (linear, 1 amplitude) in a Tecan F200Pro microplate reader (Tecan, USA).

Random mutagenesis library of PMDsc was cloned into a ColE1-based plasmid under control of a Tet promoter ($P_{Tet}$) and transformed into E. coli DH1 strains harboring pBbA5c-MevTo-BBa1002-pTrc-MKco-EcIdi-MtIPK (JBEI-15350). DH1 strains with the random mutagenesis library were re-suspended and diluted to OD 0.2 in 100 µL of EZ-Rich medium containing 1% glucose, 0.1 mM IPTG, 30 µg/mL Cm, and 100 µg/mL Amp, 50 µM fosmidomycin, and 100 nM anhydrotetracycline (aTc). Cell cultures were prepared in 96-well plates (Nunc) and incubated at 37° C. with shaking speed of 173 rpm (linear, 1 amplitude) in a Tecan F200Pro microplate reader (Tecan, USA). After 24 hours of incubation (Day 2), the overnight cultures were diluted 100-fold in 2 mL EZ-rich medium containing 1% glucose, to recover surviving strains. The overnight cultures were challenged again by diluting them to OD 0.05 in 100 µL EZ-rich medium containing 1% glucose, 0.1 mM IPTG, 50 µM fosmidomycin, and 10 nM aTc. The 96-well plates were incubated at 37° C. at a shaking speed of 173 rpm (linear, 1 amplitude) in a Tecan F200Pro microplate reader (Tecan, USA), and cell cultures were subsequently diluted to OD 0.05 once growth reached the exponential phase. The dilutions were continued until the growth rate of all libraries reached that of R74H.

Isopentenol Production in E. Coli

For isopentenol production, E. coli DH1 was transformed with two plasmids (JBEI-9310 and pTrc99a plasmids expression PMDsc variants), and isopentenol production was performed as previously described (Kang et al., 2016). Briefly, seed cultures were prepared from single colonies, grown overnight and diluted to OD 0.05 in EZ-Rich defined medium (Teknova, USA) containing 10 g/L glucose (1%, w/v), 100 µg/mL ampicillin, and 30 µg/mL chloramphenicol. Cell cultures (5 mL) were grown at 37° C. at a shaking speed of 200 rpm. At $OD_{600}$ of 0.4-0.6, 0.5 mM IPTG was added to the cell cultures to induce expression of genes from the two plasmids, and the cultures were incubated at 30° C. and 200 rpm for up to 48 hours. For isopentenol quantitation, an aliquot of cell cultures (270 µL) was combined with 270 µL ethyl acetate containing 1-butanol (30 mg/L) as an internal standard, and the mixture were vigorously mixed for 15 min to extract isopentenol in the cell culture to the ethyl acetate. After extraction, cells were centrifuged at 20,000×g for 2 minutes, and 100 µL of the ethyl acetate layer was diluted 5-fold in ethyl acetate containing 1-butanol (30 mg/L). An aliquot (1 µL) of each of the diluted samples was analyzed by Thermo GC-FID equipped with DB-WAX column (Agilent, USA).

Protein Expression and Purification

Protein expression and purification protocols were performed in a manner similar previously published with minor modifications (Kang et al., 2016). Namely, PMDsc mutant plasmids were harbored in the Rosetta (DE3) bacterial strain as opposed to the BL21(DE3) strain. Seed cultures were grown and harvested in Terrific Broth medium with 2% glycerol containing 50 mg/L kanamycin and 30 mg/L chloramphenicol. Cells were initially grown at 37° C. with shaking at 200 rpm until the $OD_{600}$ reached 0.6-0.8. Thereafter, the cell cultures were induced with 0.5 mM IPTG and incubated overnight at 18° C.

Cells were pelleted by centrifuging at 5,524×g for 10 minutes at 4° C.; cell lysis was prompted by suspending cell pellets in 50 mM Tris-HCl (pH 8.2) containing 300 mM NaCl, 10 mM imidazole, and 1 mg/mL lysozyme (Sigma). The lysates were centrifuged for 30 minutes at 15,344×g and loaded directly onto a 1 mL HisTrap FF column. After washing with 15 column volumes of lysis buffer, the His-tagged PMDsc was eluted using 50 mM Tris-HCl (pH 7.5), 300 mM NaCl, and 240 mM imidazole. The eluent proteins were concentrated to 100-500 µM using a Millipore 30,000 MWCO spin column, snap frozen in liquid nitrogen, and stored at −80° C. The activity for wild type PMDsc containing higher salt concentrations was measured to be within error of that found for PMDsc prepared with a desalting step (Kang et al., 2016), which was omitted along with supplementation of purified enzyme with dithiothreitol and glycerol.

Enzyme Characterization and Kinetics of PMD

In vitro enzyme kinetics of PMDsc were performed as described in the previous study (Kang et al., 2016). Briefly, enzymatic activity was determined by a spectrophotometric assay quantifying ADP product formation via the pyruvate kinase/lactate dehydrogenase coupled enzyme assay. Assay mixtures were prepared in 150 µL total volume containing 50 mM HEPES-KOH (pH 7.5), 10 mM $MgCl_2$, 400 µM phosphoenolpyruvate, 400 µM NADH, 4 mM ATP, and 25 U of pyruvate kinase/lactate dehydrogenase. The reaction was initiated by enzyme after incubating PMDsc substrate and cofactor for fifteen minutes with coupled assay components. The MVAP was varied from 0.100-4.0 mM, and the reaction velocity was determined by monitoring the absorbance at 340 nm in a Spectramax 384plus microplate reader (Molecular Devices, USA). To obtain kinetic data relevant to non-competitive substrate inhibition, MVAP was varied from 0.100-100 mM. Enzyme concentration ($\varepsilon$=56,630 $M^{-1}$ $cm^{-1}$) was determined spectrophotometrically at 280 nm with a NanoDrop ND-1000 spectrophotometer. $k_{cat}$ and $K_M$ were derived for PMDsc mutants by fitting the initial velocities measured from 0.100-4.0 mM MVAP to the Michaelis-Menten equation; $K_I$ was determined for select mutants by fitting initial velocities measured from 0.100-100 mM MVAP to the non-competitive substrate inhibition equation. All kinetic analysis was performed in Graphpad Prism, version 7.0a.

REFERENCES CITED

Adolfsen, K. J., Brynildsen, M. P., 2015. Futile cycling increases sensitivity toward oxidative stress in *Escherichia coli*. Metab Eng. 29, 26-35.

Atsumi, S., Hanai, T., Liao, J. C., 2008. Non-fermentative pathways for synthesis of branched-chain higher alcohols as biofuels. Nature. 451, 86-U13.

Barta, M. L., McWhorter, W. J., Miziorko, H. M., Geisbrecht, B. V., 2012. Structural basis for nucleotide binding and reaction catalysis in mevalonate diphosphate decarboxylase. Biochemistry. 51, 5611-21.

Barta, M. L., Skaff, D. A., McWhorter, W. J., Herdendorf, T. J., Miziorko, H. M., Geisbrecht, B. V., 2011. Crystal structures of *Staphylococcus epidermidis* mevalonate diphosphate decarboxylase bound to inhibitory analogs reveal new insight into substrate binding and catalysis. J Biol Chem. 286, 23900-10.

Beller, H. R., Lee, T. S., Katz, L., 2015. Natural products as biofuels and bio-based chemicals: fatty acids and isoprenoids. Nat Prod Rep. 32, 1508-26.

Bonanno, J. B., Edo, C., Eswar, N., Pieper, U., Romanowski, M. J., Ilyin, V., Gerchman, S. E., Kycia, H., Studier, F. W., Sali, A., Burley, S. K., 2001. Structural genomics of enzymes involved in sterol/isoprenoid biosynthesis. Proc Natl Acad Sci USA. 98, 12896-901.

Chen, M., Poulter, C. D., 2010. Characterization of thermophilic archaeal isopentenyl phosphate kinases. Biochemistry. 49, 207-17.

Chou, H. H., Keasling, J. D., 2012. Synthetic pathway for production of five-carbon alcohols from isopentenyl diphosphate. Applied and environmental microbiology. 78, 7849-55.

Cohen, B. E., 2014. Functional linkage between genes that regulate osmotic stress responses and multidrug resistance transporters: challenges and opportunities for antibiotic discovery. Antimicrob Agents Chemother. 58, 640-6.

Funke, M., Buchenauer, A., Mokwa, W., Kluge, S., Hein, L., Müller, C., Kensy, F., Büchs, J., 2010. Bioprocess control in microscale: scalable fermentations in disposable and user-friendly microfluidic systems. Microb Cell Fact. 9, 86.

George, K. W., Alonso-Gutierrez, J., Keasling, J. D., Lee, T. S., 2015a. Isoprenoid drugs, biofuels, and chemicals—artemisinin, farnesene, and beyond. Adv Biochem Eng Biotechnol. 148, 355-89.

George, K. W., Chen, A., Jain, A., Batth, T. S., Baidoo, E. E., Wang, G., Adams, P. D., Petzold, C. J., Keasling, J. D., Lee, T. S., 2014. Correlation analysis of targeted proteins and metabolites to assess and engineer microbial isopentenol production. Biotechnology and bioengineering. 111, 1648-58.

George, K. W., Thompson, M. G., Kang, A., Baidoo, E., Wang, G., Chan, L. J., Adams, P. D., Petzold, C. J., Keasling, J. D., Lee, T. S., 2015b. Metabolic engineering for the high-yield production of isoprenoid-based C(5) alcohols in *E. coli*. Sci Rep. 5, 11128.

Gogerty, D. S., Bobik, T. A., 2010. Formation of isobutene from 3-hydroxy-3-methylbutyrate by diphosphomevalonate decarboxylase. Applied and environmental microbiology. 76, 8004-10.

Hengge, R., 2008. The two-component network and the general stress sigma factor RpoS (sigma S) in *Escherichia coli*. Adv Exp Med Biol. 631, 40-53.

Heuston, S., Begley, M., Gahan, C. G., Hill, C., 2012. Isoprenoid biosynthesis in bacterial pathogens. Microbiology. 158, 1389-401.

Kang, A., George, K. W., Wang, G., Baidoo, E., Keasling, J. D., Lee, T. S., 2016. Isopentenyl diphosphate (IPP)-bypass mevalonate pathways for isopentenol production. Metab Eng. 34, 25-35.

Krepkiy, D., Miziorko, H. M., 2004. Identification of active site residues in mevalonate diphosphate decarboxylase: implications for a family of phosphotransferases. Protein Sci. 13, 1875-81.

Krepkiy, D. V., Miziorko, H. M., 2005. Investigation of the functional contributions of invariant serine residues in yeast mevalonate diphosphate decarboxylase. Biochemistry. 44, 2671-7.

Lange, B. M., Croteau, R., 1999. Isopentenyl diphosphate biosynthesis via a mevalonate-independent pathway: isopentenyl monophosphate kinase catalyzes the terminal enzymatic step. Proc Natl Acad Sci USA. 96, 13714-9.

Lee, T. S., Krupa, R. A., Zhang, F., Hajimorad, M., Holtz, W. J., Prasad, N., Lee, S. K., Keasling, J. D., 2011. BglBrick vectors and datasheets: A synthetic biology platform for gene expression. J Biol Eng. 5, 12.

Liu, H. W., Wang, Y., Tang, Q., Kong, W. T., Chung, W. J., Lu, T., 2014. MEP pathway—mediated isopentenol production in metabolically engineered Escherichia coli. Microb Cell Fact. 13.

Mack, J. H., Rapp, V. H., Broeckelmann, M., Lee, T. S., Dibble, R. W., 2014. Investigation of biofuels from microorganism metabolism for use as anti-knock additives. Fuel. 117, 939-943.

Martin, V. J., Pitera, D. J., Withers, S. T., Newman, J. D., Keasling, J. D., 2003. Engineering a mevalonate pathway in Escherichia coli for production of terpenoids. Nat Biotechnol. 21, 796-802.

Martinez, J. L., Baquero, F., 2000. Mutation frequencies and antibiotic resistance. Antimicrob Agents Chemother. 44, 1771-7.

McCullum, E. O., Williams, B. A., Zhang, J., Chaput, J. C., 2010. Random mutagenesis by error-prone PCR. Methods Mol Biol. 634, 103-9.

Packer, M. S., Liu, D. R., 2015. Methods for the directed evolution of proteins. Nat Rev Genet. 16, 379-94.

Saraste, M., Sibbald, P. R., Wittinghofer, A., 1990. The P-loop—a common motif in ATP- and GTP-binding proteins. Trends Biochem Sci. 15, 430-4.

Sun, Y., Fukamachi, T., Saito, H., Kobayashi, H., 2011. ATP requirement for acidic resistance in Escherichia coli. J Bacteriol. 193, 3072-7.

Weerasinghe, S., Samantha Dassanayake, R., 2010. Simulation of structural and functional properties of mevalonate diphosphate decarboxylase (MVD). J Mol Model. 16, 489-98.

Zhang, B., Watts, K. M., Hodge, D., Kemp, L. M., Hunstad, D. A., Hicks, L. M., Odom, A. R., 2011. A second target of the antimalarial and antibacterial agent fosmidomycin revealed by cellular metabolic profiling. Biochemistry. 50, 3570-7.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method to identify a second or mutant phosphomevalonate decarboxylase (PMD) with a higher PMD activity compared to a first PMD, comprising (a) culturing a medium comprising a first host cell expressing the first PMD and a second host cell expressing the second or mutant PMD wherein the first and second host cells have their respective PMD enzymatic activities coupled to the growth rates of the host cells, wherein the host cell is microorganism which produces IPP via the MEP pathway transformed with one or more polynucleotides encoding 3-hydroxy-3-methylglutaryl-coenzyme A reductase (HMGR), 3-hydroxy-3-methyl-glutaryl-coenzyme A synthase (HMGS), mevalonate kinase (MK) and isopentenyl phosphate kinase (IPK) and treated with fosmidomycin, and (b) identifying the second host cell that has a higher growth rate than the first host cell, thereby identifying the second or mutant PMD having a higher PMD activity; wherein the host cell is a prokaryotic cell.

2. The method of claim 1, wherein the prokaryotic cell is an *Escherichia, Enterobacter, Azotobacter, Erwinia, Bacillus, Pseudomonas, Klebsielia, Proteus, Salmonella, Serratia, Shigella, Rhizobia, Vitreoscilla, Paracoccus*, or *Clostridia* cell.

3. The method of claim 2, wherein the prokaryotic cell is an *Escherichia* cell.

4. The method of claim 3, wherein the *Escherichia* cell is an *Escherichia coli* cell.

\* \* \* \* \*

SEQUENCE LISTING

<160> NUMBER OF SEQ ID NOS: 2

<210> SEQ ID NO 1
<211> LENGTH: 396
<212> TYPE: PRT
<213> ORGANISM: Saccharomyces cerevisiae

<400> SEQUENCE: 1

```
Met Thr Val Tyr Thr Ala Ser Val Thr Ala Pro Val Asn Ile Ala Thr
1               5                   10                  15

Leu Lys Tyr Trp Gly Lys Arg Asp Thr Lys Leu Asn Leu Pro Thr Asn
            20                  25                  30

Ser Ser Ile Ser Val Thr Leu Ser Gln Asp Asp Leu Arg Thr Leu Thr
        35                  40                  45

Ser Ala Ala Thr Ala Pro Glu Phe Glu Arg Asp Thr Leu Trp Leu Asn
    50                  55                  60

Gly Glu Pro His Ser Ile Asp Asn Glu Arg Thr Gln Asn Cys Leu Arg
65                  70                  75                  80

Asp Leu Arg Gln Leu Arg Lys Glu Met Glu Ser Lys Asp Ala Ser Leu
                85                  90                  95

Pro Thr Leu Ser Gln Trp Lys Leu His Ile Val Ser Glu Asn Asn Phe
            100                 105                 110

Pro Thr Ala Ala Gly Leu Ala Ser Ser Ala Ala Gly Phe Ala Ala Leu
        115                 120                 125

Val Ser Ala Ile Ala Lys Leu Tyr Gln Leu Pro Gln Ser Thr Ser Glu
    130                 135                 140

Ile Ser Arg Ile Ala Arg Lys Gly Ser Gly Ser Ala Cys Arg Ser Leu
145                 150                 155                 160

Phe Gly Gly Tyr Val Ala Trp Glu Met Gly Lys Ala Glu Asp Gly His
                165                 170                 175

Asp Ser Met Ala Val Gln Ile Ala Asp Ser Ser Asp Trp Pro Gln Met
            180                 185                 190

Lys Ala Cys Val Leu Val Val Ser Asp Ile Lys Lys Asp Val Ser Ser
```

```
                195                 200                 205
Thr Gln Gly Met Gln Leu Thr Val Ala Thr Ser Glu Leu Phe Lys Glu
210                 215                 220

Arg Ile Glu His Val Val Pro Lys Arg Phe Glu Val Met Arg Lys Ala
225                 230                 235                 240

Ile Val Glu Lys Asp Phe Ala Thr Phe Ala Lys Glu Thr Met Met Asp
                245                 250                 255

Ser Asn Ser Phe His Ala Thr Cys Leu Asp Ser Phe Pro Pro Ile Phe
                260                 265                 270

Tyr Met Asn Asp Thr Ser Lys Arg Ile Ile Ser Trp Cys His Thr Ile
                275                 280                 285

Asn Gln Phe Tyr Gly Glu Thr Ile Val Ala Tyr Thr Phe Asp Ala Gly
290                 295                 300

Pro Asn Ala Val Leu Tyr Tyr Leu Ala Glu Asn Glu Ser Lys Leu Phe
305                 310                 315                 320

Ala Phe Ile Tyr Lys Leu Phe Gly Ser Val Pro Gly Trp Asp Lys Lys
                325                 330                 335

Phe Thr Thr Glu Gln Leu Glu Ala Phe Asn His Gln Phe Glu Ser Ser
                340                 345                 350

Asn Phe Thr Ala Arg Glu Leu Asp Leu Glu Leu Gln Lys Asp Val Ala
                355                 360                 365

Arg Val Ile Leu Thr Gln Val Gly Ser Gly Pro Gln Glu Thr Asn Glu
370                 375                 380

Ser Leu Ile Asp Ala Lys Thr Gly Leu Pro Lys Glu
385                 390                 395

<210> SEQ ID NO 2
<211> LENGTH: 327
<212> TYPE: PRT
<213> ORGANISM: Staphylococcus epidermidis

<400> SEQUENCE: 2

Met Val Lys Ser Gly Lys Ala Arg Ala His Thr Asn Ile Ala Leu Ile
1               5                   10                  15

Lys Tyr Trp Gly Lys Ala Asp Glu Thr Tyr Ile Ile Pro Met Asn Asn
                20                  25                  30

Ser Leu Ser Val Thr Leu Asp Arg Phe Tyr Thr Glu Thr Lys Val Thr
                35                  40                  45

Phe Asp Pro Asp Phe Thr Glu Asp Cys Leu Ile Leu Asn Gly Asn Glu
50                  55                  60

Val Asn Ala Lys Glu Lys Glu Lys Ile Gln Asn Tyr Met Asn Ile Val
65                  70                  75                  80

Arg Asp Leu Ala Gly Asn Arg Leu His Ala Arg Ile Glu Ser Glu Asn
                85                  90                  95

Tyr Val Pro Thr Ala Ala Gly Leu Ala Ser Ser Ala Ser Ala Tyr Ala
                100                 105                 110

Ala Leu Ala Ala Ala Cys Asn Glu Ala Leu Ser Leu Asn Leu Ser Asp
                115                 120                 125

Thr Asp Leu Ser Arg Leu Ala Arg Arg Gly Ser Gly Ser Ala Ser Arg
130                 135                 140

Ser Ile Phe Gly Gly Phe Ala Glu Trp Glu Lys Gly His Asp Asp Leu
145                 150                 155                 160

Thr Ser Tyr Ala His Gly Ile Asn Ser Asn Gly Trp Glu Lys Asp Leu
                165                 170                 175
```

-continued

```
Ser Met Ile Phe Val Val Ile Asn Asn Gln Ser Lys Lys Val Ser Ser
            180             185             190

Arg Ser Gly Met Ser Leu Thr Arg Asp Thr Ser Arg Phe Tyr Gln Tyr
        195             200             205

Trp Leu Asp His Val Asp Glu Asp Leu Asn Glu Ala Lys Glu Ala Val
        210             215             220

Lys Asn Gln Asp Phe Gln Arg Leu Gly Glu Val Ile Glu Ala Asn Gly
225             230             235             240

Leu Arg Met His Ala Thr Asn Leu Gly Ala Gln Pro Pro Phe Thr Tyr
            245             250             255

Leu Val Gln Glu Ser Tyr Asp Ala Met Ala Ile Val Glu Gln Cys Arg
            260             265             270

Lys Ala Asn Leu Pro Cys Tyr Phe Thr Met Asp Ala Gly Pro Asn Val
        275             280             285

Lys Val Leu Val Glu Lys Lys Asn Lys Gln Ala Val Met Glu Gln Phe
        290             295             300

Leu Lys Val Phe Asp Glu Ser Lys Ile Ile Ala Ser Asp Ile Ile Ser
305             310             315             320

Ser Gly Val Glu Ile Ile Lys
            325
```